(12) United States Patent
Tsutsui et al.

(10) Patent No.: US 8,221,373 B2
(45) Date of Patent: Jul. 17, 2012

(54) BREAST PAD AND METHOD FOR PRODUCING THE SAME

(75) Inventors: Katsushi Tsutsui, Tokyo (JP);
Masahiko Fujishiro, Tokyo (JP);
Hidekazu Okuno, Tokyo (JP)

(73) Assignee: Pigeon Corporation, Tokyo (JP)

( * ) Notice: Subject to any disclaimer, the term of this patent is extended or adjusted under 35 U.S.C. 154(b) by 950 days.

(21) Appl. No.: 12/092,376

(22) PCT Filed: Oct. 24, 2006

(86) PCT No.: PCT/JP2006/321176
§ 371 (c)(1),
(2), (4) Date: Sep. 3, 2008

(87) PCT Pub. No.: WO2007/052498
PCT Pub. Date: May 10, 2007

(65) Prior Publication Data
US 2009/0131900 A1    May 21, 2009

(30) Foreign Application Priority Data

Nov. 1, 2005 (JP) ................................. 2005-318322

(51) Int. Cl.
*A61F 13/15* (2006.01)
(52) U.S. Cl. .................................. 604/385.07; 604/380
(58) Field of Classification Search .................. 604/380, 604/385.07; 450/18, 36, 37
See application file for complete search history.

(56) References Cited

U.S. PATENT DOCUMENTS 2,891,544 A * 6/1959 London ........................ 604/379
4,674,510 A    6/1987 Sneider
5,683,286 A * 11/1997 Kielland ........................ 450/37
5,843,062 A    12/1998 Reidmiller
(Continued)

FOREIGN PATENT DOCUMENTS
GB          904580 A    8/1962
(Continued)

OTHER PUBLICATIONS

Chinese Office Action for Chinese Patent Application No. 200680040889X dated Jun. 1, 2009.
(Continued)

*Primary Examiner* — Lynne Anderson
(74) *Attorney, Agent, or Firm* — Kenealy Vaidya LLP

(57) ABSTRACT

A breast-milk pad can be produced relatively easily, such that it reduces an uncomfortable sensation to the skin surface of a user, and has excellent shape retention properties. A method for producing the breast-milk pad is also disclosed. The breast-milk pad can include a material that is made up by stacking: a back sheet that prevents permeation of liquid; a top sheet that contacts the body; and an absorber that is disposed between the back sheet and the top sheet. The top sheet and the back sheet are bonded to each other in an outer peripheral portion. Cutout portions obtained by cutting the absorber can be formed in positions facing each other at the outer peripheral portion such that cutout width of each of the cutout portions gradually narrows down inwardly. The top sheet and the back sheet can be bonded to each other on the inner side between the cutout portions, and the breast-milk pad can further include bonding portions for bonding inner surfaces of the top sheet together, which are superposed at each of the cutout portions, in a state in which the product is folded up along a folding line connecting the cutout portions facing each other so that the top sheet forms the inner surfaces.

17 Claims, 15 Drawing Sheets

U.S. PATENT DOCUMENTS

| | | |
|---|---|---|
| 6,390,886 B1 | 5/2002 | Roberts |
| 6,945,966 B2 * | 9/2005 | Mikami ........................ 604/346 |
| 7,416,544 B2 * | 8/2008 | Sakaguchi et al. ....... 604/385.07 |

FOREIGN PATENT DOCUMENTS

| | | | |
|---|---|---|---|
| GB | 2 064 961 A | 6/1981 |
| JP | 59143434 | 9/1984 |
| JP | 329284 | 6/1991 |
| JP | 4209803 | 7/1992 |
| JP | 749603 | 5/1995 |
| JP | 200111705 | 1/2001 |
| JP | 2003-138404 A | 5/2003 |
| JP | 2004-332178 A | 11/2004 |
| JP | 2004332178 | 11/2004 |

OTHER PUBLICATIONS

Supplementary European Search Report for EP Application No. 06 82 2156 dated Nov. 11, 2010.

* cited by examiner

FIG. 11
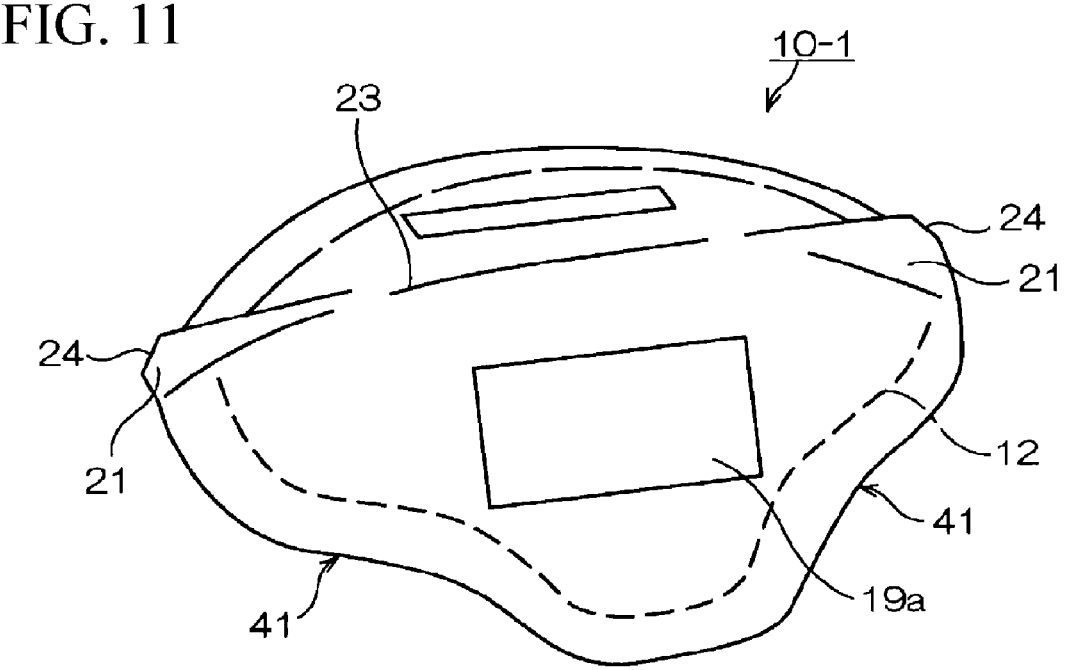
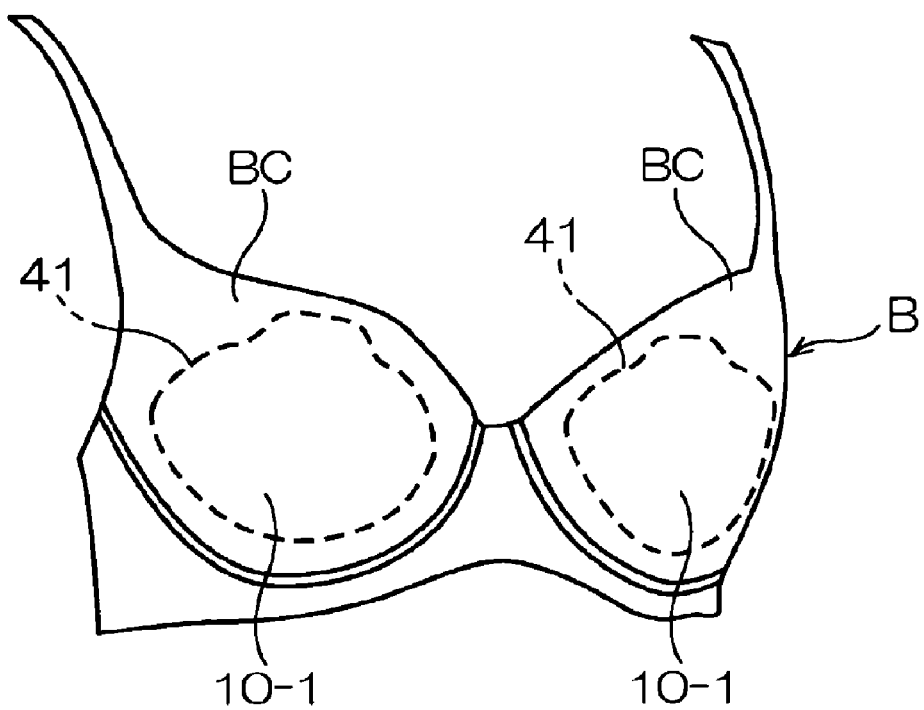
FIG. 12

FIG. 23
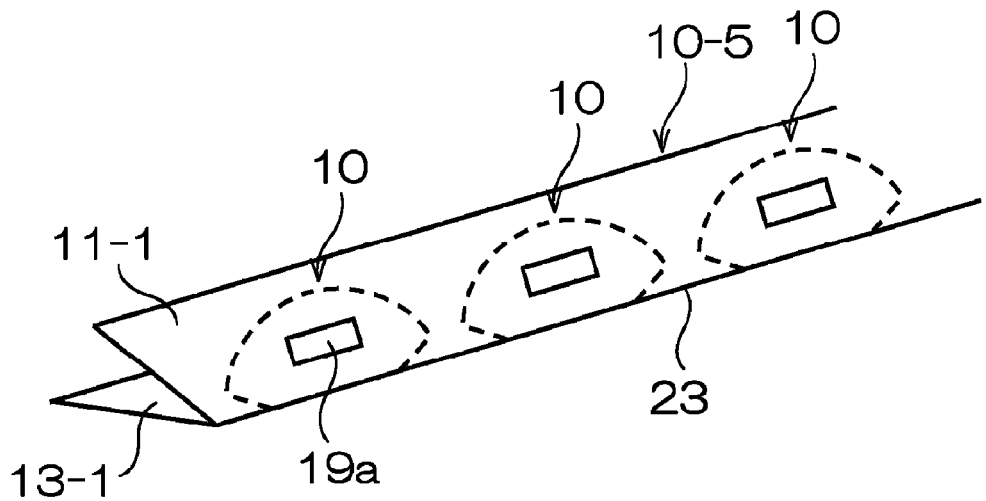
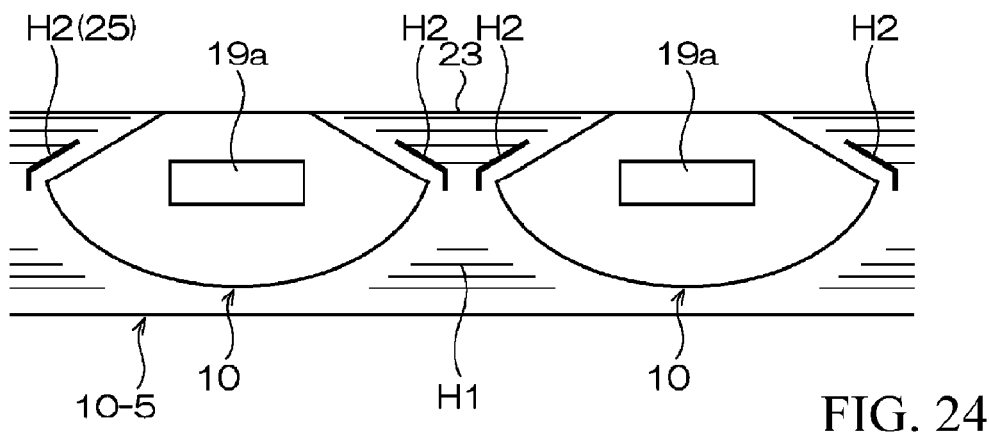
FIG. 24
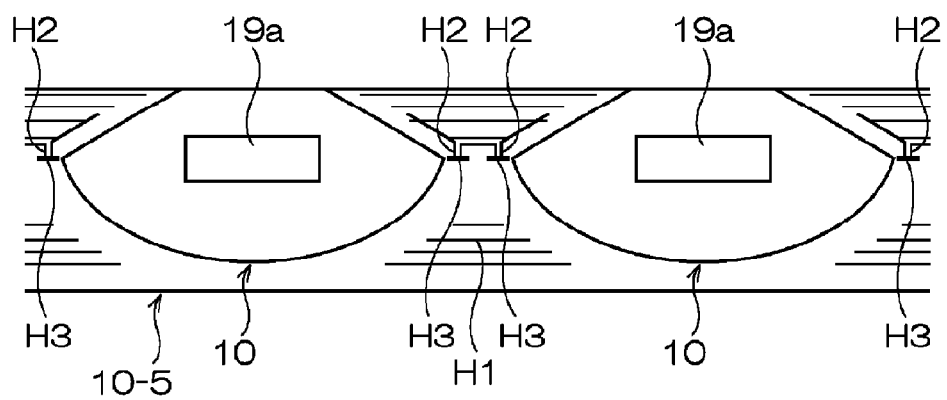
FIG. 25

BREAST PAD AND METHOD FOR PRODUCING THE SAME

BACKGROUND

This application is a National Stage application filed under 35 U.S.C. §371 of PCT/JP2006/321176 filed on Oct. 24, 2006 which claims priority to Japanese Patent Application No. 2005-318322 filed on Nov. 1, 2005, which are both hereby incorporated in their entirety by reference.

TECHNICAL FIELD

The presently disclosed subject matter relates to a breast-milk pad interposed between underwear, such as a brassiere, and a breast of a breast-feeding mother, and to the improvement of a method for producing the breast-milk pad.

DESCRIPTION OF CONVENTIONAL ART

Most conventional breast-milk pads are formed into, for example, a circular domical shape by using a material capable of absorbing breast milk, so that these breast pads can be attached closely to and cover the front of a breast of a user.

One example of the conventional techniques for forming this dome shape is to heat a circular material, which is formed flat on a top sheet on an outer surface by using polyethylene laminated paper or other thermal deformation material, and at the same time press the circular material against a dome mold to thermoform the abovementioned dome shape. Such a product does not have sufficient shape retention properties, causing a deterioration of fitting properties and displacement when the dome part loses its shape. Therefore, there is a problem in that the breast milk leaks out without being absorbed and can thus smudge clothes.

On the other hand, there is a product in which gatherings made of a rubber or other elastic body are provided in a vertical direction on each side of a product having a circular or approximately circular shape, whereby good shape retention properties and a dome shape can be obtained (see Patent Document 1 listed below).

There is also a product in which a circular absorber is cut along one of its radii and the fan-shaped area obtained from the cut section is superposed and bonded to form a low conical dome (see Patent Document 2 listed below).

There are also a number of techniques having substantially the same configuration (see Patent Documents 3, 4 and 5 listed below). A drawback of each of these products is that the productivity is low and the above mentioned bonding has to be performed by the user, which is troublesome.

Therefore, a product having a different configuration is known in which a sheet is folded into two and both side edges are cut and bonded together so that the both side edges open wide toward the opening from the folded side (see Patent Document 6 listed below).

In another configuration, there is a breast-milk pad in which fan-shaped cutout portions are formed along radii of a circular absorber that face each other, and an elastic body is disposed in each cutout portion in a traverse direction so as to narrow the fan-shaped cutout portion, so that the absorber is fitted over a breast as the elastic body contracts when applied to the breast (see Patent Document 7 listed below).

Patent Document 1: Japanese Patent Application Laid-open No. 2004-11705

Patent Document 2: Unexamined Utility Model Application Pub. No. S59-143434

Patent Document 3: Examined Utility Model Application Publication No. H3-29284

Patent Document 4: Japanese Patent Application Laid-open No. H4-209803

Patent Document 5: U.S. Pat. No. 6,390,886

Patent Document 6: Japanese Patent Application Laid-open No. 2004-332178

Patent Document 7: Japanese Published Examined Patent App. No. H7-49603

The breast-milk pad of Patent Document 6 uses a thin sheet in place of an absorber, and thus a drawback thereof is that a sufficient amount breast milk cannot be absorbed and the deep conical dome shape lacks fitting properties. Therefore, due to the complex shape of this product, not only is the production thereof complicated, but also the bonding portions might be opened during use if the absorber is disposed in this configuration.

In addition, the breast-milk pad of Patent Document 7 has a complex structure in which an elastic body is applied to the cutout, and the cutout is fixed, hence the problems are that it is difficult to produce this product and a hard and uncomfortable sensation may be felt when the section provided with the elastic body contacts the skin of the user.

SUMMARY

The presently disclosed subject matter has been contrived in order to address or attempt to solve such problems, features and characteristics, and an aspect thereof includes a breast-milk pad, which can be produced relatively easily, does not provide an uncomfortable sensation to the skin surface of a user, and has excellent shape retention properties, and a method for producing the breast-milk pad.

The abovementioned aspect can be achieved by a pad including a breast-milk pad having a material made up by stacking: a back sheet that prevents permeation of liquid; a liquid permeable top sheet that is disposed on each side contacting a body; and an absorber that is disposed between the back sheet and the top sheet to absorb and retain the liquid permeating the top sheet, wherein the top sheet and the back sheet are bonded to each other in an outer peripheral portion, cutout portions obtained by cutting the absorber are formed in positions facing each other at the outer peripheral portion such that cutout width of each of the cutout portions gradually narrows down inwardly, the top sheet and the back sheet are bonded to each other on an inner side between the cutout portions, and the breast-milk pad has bonding portions for bonding inner surfaces of the top sheet together, which are superposed at each of cutout portions, in a state in which the product is folded up along a folding line connecting the cutout portions facing each other so that the top sheet forms the inner surfaces.

The configuration of a first embodiment of the disclosed subject matter is a product in which the absorber is stored between the top sheet and the back sheet, wherein the top sheet and the back sheet are bonded to each other at the outer peripheral portion of the breast-milk pad to cover the absorber without exposing it to the outside.

The internally positioned absorber has a special aspect. Specifically, the absorber has cutout portions that are provided respectively in the positions facing each other at the outer peripheral portion. Each of these cutout portions is formed by cutting out the absorber in such a manner that the cutout width of each cutout portion gradually narrows down inwardly.

Another aspect is that the top sheet and the back sheet can be bonded to each other on the inner side between the cutout portions and that these members are bonded to each other such as to enter the cutout portions, and the breast-milk pad further has the bonding portions for bonding the inner surfaces of the top sheet together, which are superposed at the cutout portions, in a state in which the top sheet is folded up along the folding line connecting the cutout portions facing each other so that the top sheet forms the inner surfaces.

In this manner, because the inner surfaces of the top sheet that are superposed at the positions of the cutout portions are bonded to each other along the double-folding line, it is not necessary to superpose and bond the thick absorber together, and because the inner surfaces of the top sheet are bonded to each other along the folded position thereof, the breast-milk pad can be produced relatively easily.

Moreover, because the dome shape is not created by bonding the absorber, the bonding of the top sheets that support the dome shape does not change even when the absorber part is somewhat flattened by absorbing the liquid during use, hence the dome shape is prevented from being extremely unbalanced and the fitting properties are prevented from being damaged.

Furthermore, because the gatherings are provided in the section abutting on the skin surface of the user, and the section hardened by heat does not contact the skin surface, uncomfortable sensation is extremely small. In addition, because those gatherings used in the conventional techniques are not used to form the dome shape, it is not necessary to use an elastic body such as a rubber piece in the interior, hence the production of the breast-milk pad becomes simple.

The second aspect of the disclosed subject matter can include features from the first aspect, and the top sheet can have a thermal fusion material, and be heated from the back sheet side and fused at the cutout portions at the time of folding, whereby the bonding portions are formed.

According to the configuration of the second aspect of the disclosed subject matter, the bonding portions that support the dome shape can be created in a heat sealing process performed on the cutout portions positioned on the folded folding line. Also, since an adhesive may not be used for the bonding, uncomfortable feeling is generated by an adhesive interposed at a predetermined volume.

The third aspect of the disclosed subject matter can include features from the first or second aspect of the disclosed subject matter, and angled portions of the bonding portions can be chamfered to provide chamfered portions.

According to the third aspect of the disclosed subject matter, when an angled portion exists in an end of the folding line, the angled portion abuts on the inner surface of underwear, such as a brassiere, and is folded back to the skin side, possibly causing an uncomfortable sensation. However, such uncomfortable sensation is not generated because the angled portion is chamfered.

In a fourth aspect of the disclosed subject matter which can include features from any of the first through third aspects of the disclosed subject matters, an absorbing/dispersing layer can have rougher density than the absorber and can be provided between the absorber and the top sheet, and the absorbing/dispersing layer can be disposed on an inner side of each bonding portion.

According to the fourth aspect of the disclosed subject matter, the initial absorption speed of the breast milk can be increased so that the breast milk can be dispersed to the entire absorber and absorbed by the absorbing/dispersing layer. The breast milk can be prevented from leaking along the surface of the top sheet, and the absorbed breast milk returning to the skin side to provide an uncomfortable feeling, wetting back, can also be prevented. Moreover, due to the rough density of the absorbing/dispersing layer, it can feel soft to the skin and the fitting properties can be improved.

In a fifth aspect of the disclosed subject matter, which can include features from the first through fourth aspects of the disclosed subject matter, the cutout portions are formed in two sections facing each other at the outer edge portion, and the product is folded into two along the folding line.

According to the configuration of the fifth aspect of the disclosed subject matter, after the breast-milk pad is produced, the breast-milk pad is folded into two and flattened when storing it in wrapping means so that compact storage can be realized, but the dome shape can be realized easily without damaging the structure that supports the dome shape and simply by opening the double-fold part when the user uses the breast-milk pad, hence it can be used simply.

The sixth aspect of the disclosed subject matter can include features from any of the first through fourth aspects of the disclosed subject matter, and the cutout portions can be formed at four sections facing each other at the outer edge portion so as to obtain two pairs of cutout portions. Thus, by folding along the folding line connecting each pair of cutout portions facing each other such that the top sheet forms the inner surfaces, the entire product is folded into three.

According to the configuration of the sixth aspect of the disclosed subject matter, the product is folded into three so that it can be stored compactly, and the three-dimensional dome shape can be created by the two folding lines.

In the seventh aspect of the disclosed subject matter, which can include features from any of the first through sixth aspects of the disclosed subject matter, one or a plurality of outer edge cut portions are formed in the outer edge portion of the product by removing the stacked material.

According to the configuration of the seventh aspect of the disclosed subject matter, when the breast-milk pad is attached under the underwear such as a brassiere, a part of the product is prevented from being exposed from the underwear by forming the outer edge cut portion and thus from being recognized from the outside.

The eighth aspect of the disclosed subject matter can include features from any of the first through seventh aspects of the disclosed subject matter, when the folded product is opened into substantially a dome shape, the cutout portions is provided with a sealing section that forms the bonding portions at a position where a gap between the absorbers is almost invisible.

According to the configuration of the eighth aspect of the disclosed subject matter, in the dome-shaped breast-milk pad obtained by opening the folded product, the area with no absorber is made smallest by the sealing section, and extruded breast milk can be absorbed securely without exposing the part incapable of absorbing and retaining the liquid to the top sheet side.

The ninth aspect of the disclosed subject matter can include features of any of the first through seventh aspects of the disclosed subject matter and is configured such that not only the outer edge portion where only the top sheet and the back sheet are superposed but also an area in which the absorber is interposed therebetween are sandwiched from the outside, pressed and then bonded together.

According to the configuration of the ninth aspect of the disclosed subject matter, the pressed bonding portions in the outer edge portion in which only the top sheet and the back sheet are superposed are squashed and hardened more than necessary, whereby an uncomfortable sensation is prevented from occurring upon contacting the user's skin, and breakage or other damage to the material of the outer edge portion that is caused by pressing the bonding portions more than necessary can also be prevented.

In the tenth aspect of the disclosed subject matter, which can include features from any of the first through ninth aspects of the disclosed subject matter, fibers configuring the top sheet are oriented in an aligned manner along a direction in which the folding line extends.

According to the tenth configuration, when the product is applied such that the direction in which the folding line extends is disposed in a substantially horizontal direction, the fibers are oriented in a direction perpendicular to the vertical direction of the body, hence the breast milk is prevented from leaking downward along the orientations of the fibers.

The eleventh aspect of the disclosed subject matter can include features from any of the first through tenth aspects of the disclosed subject matter, and the cutout portions can have a large opening portion that is provided in an outer edge such that the angle formed by the folding line is made large, and the sealing section for reinforcing the bonding between the top sheet and the back sheet can be provided on an inner side of the large opening portion.

According to the eleventh aspect of the disclosed subject matter, when the folded product is opened, the sealing section for reinforcing the bonding is disposed in the area of the large opening portion in which the angle of the cutout portion of the absorber is made large at the outer edge side of the cutout portion, whereby the dome shape is formed, the action of keeping this shape is improved, and the section incapable of absorbing and retaining the liquid is prevented from being exposed more to the top sheet side, so that the exuded breast milk can be absorbed securely.

In the twelfth aspect of the disclosed subject matter which can include features from any of the first through eleventh aspects of the disclosed subject matter, the positions provided with the two cutout portions correspond to upper and lower positions of the product when the product is in an attached state.

According to the configuration of the twelfth aspect of the disclosed subject matter, when the two cutout portions are formed so as to correspond to the upper and lower positions, the folding line and the bonding portions are formed in the vertical direction. For this reason, the vertical rigidity of the product improves, and a situation can be prevented in which the shape of the product absorbing the breast milk can no longer be sustained and is deformed easily due to the influence of the operation of vertically moving the cup of underwear, particularly the brassiere, at the time of breast-feeding.

The thirteenth aspect of the disclosed subject matter can include features from the twelfth aspect of the disclosed subject matter, and of the two cutout portions that are formed extending inwardly from the respective outer edges so as to correspond to the upper and lower positions, the upper cutout portion is formed to be longer than the lower cutout portion, and/or the upper cutout portion is formed to be narrower than the lower cutout portion.

According to the configuration of the thirteenth aspect of the disclosed subject matter, by bonding the bonding portions that are the inner surfaces of the top sheet superposed on each other at the cutout portions, the dome shape to be formed can be conformed to the shape of a breast such that the lower part of the dome shape is steep while the upper part gently rises.

Moreover, the above aspect can be achieved by features directed to a method for producing a breast-milk pad, which can include: a molding process of molding the absorber such as to form, in each of positions facing each other at an outer peripheral portion, a cutout portion by cutting out the liquid absorber in such a manner that cutout width of the cutout portion gradually narrows down inwardly; a stacking process of disposing the molded absorber between a back sheet that prevents permeation of liquid and a liquid permeable top sheet; a sealing process of sealing the top sheet and the back sheet that constitute an outer periphery of a product; a folding process of folding the product along a folding line connecting the cutout portions facing each other so that the top sheet forms inner surfaces; a bonding process of forming bonding portions by bonding together the inner surfaces of the top sheet that are superposed at the cutout portions, in a state in which the product is folded; and a cutting process of cutting into each product unit.

Because the configuration of the fourteenth aspect of the disclosed subject matter can include the process of forming the cutout portions on the absorber without providing the inner side of the material with an elastic body such as a rubber, as well as the process of bonding the inner surfaces of the top sheet together after the folding process, the product can be formed into the dome shape. Therefore, the process of easily forming the dome shape can be realized and each of the processes can be executed continuously so that the product can be produced in large quantities.

The fifteenth aspect of the disclosed subject matter can include features from the fourteenth aspect of the disclosed subject matter, and the bonding process heat-seals an area along an outer edge of the absorber at least once, and further heat-seals the vicinity of an inner end of each cutout portion.

The configuration of the fifteenth aspect of the disclosed subject matter can realize a structure that makes it difficult to visually detect a gap formed on the absorber when the product is opened.

As described above, the presently disclosed subject matter can provide a breast-milk pad which can be produced relatively easily, alleviates uncomfortable sensation on the skin surface of a user and has excellent shape retention properties, and provides a method for producing the breast-milk pad.

BRIEF DESCRIPTION OF THE DRAWINGS

FIG. 2(*b*) is a view in which the breast-milk pad of FIG. 1 is folded into two;

FIG. 11 is a schematic perspective view of a second embodiment of a breast-milk pad according to the presently disclosed subject matter;

FIG. 12 is a view showing a state in which the breast-milk pad of FIG. 11 is used;

FIG. 23 is a view showing a folding process that is performed in a process of producing the breast-milk pad of FIG. 1;

FIG. 24 is a view showing a bonding process that is performed in a process of producing the breast-milk pad of FIG. 1;

FIG. 25 is view showing the bonding process that is performed in a process of producing the breast-milk pad of FIG. 1;

DETAILED DESCRIPTION OF EXEMPLARY EMBODIMENTS

Hereinafter, exemplary embodiments of the disclosed subject matter will be described in detail with reference to the attached drawings.

Note that the embodiments described hereinafter are concrete examples of the disclosed subject matter and thus include technical features, but the scope of the disclosed subject matter is not limited to these aspects unless otherwise specified in the following description.

Figure 1:
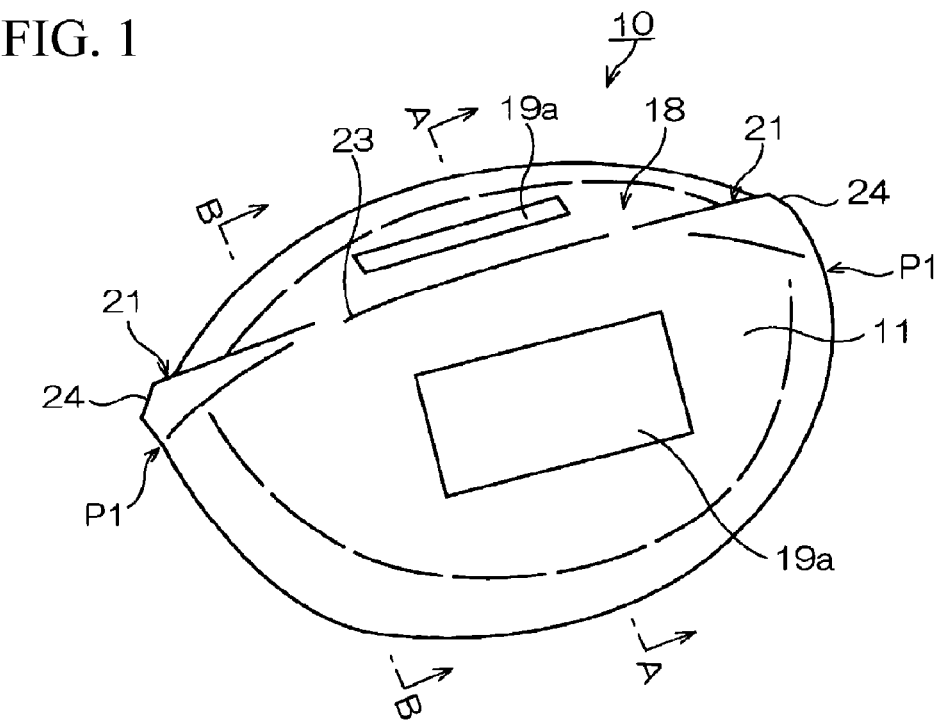
FIG. 1 is a schematic perspective view of a first embodiment of a breast-milk pad according to the presently disclosed subject matter.
Figure 2A:
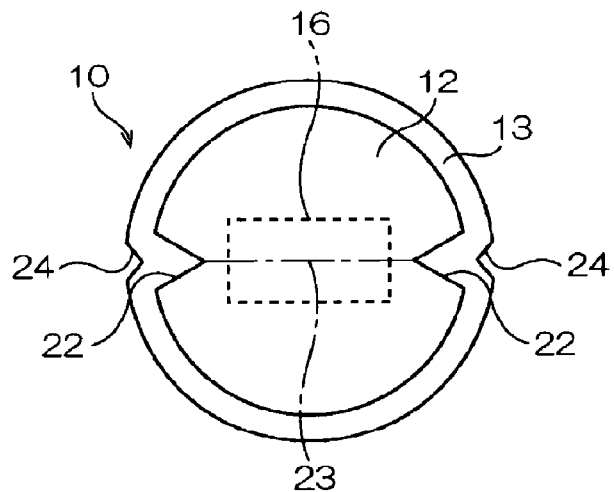
FIG. 2(*a*) is a schematic expanded view of the breast-milk pad of FIG. 1.
Figure 2B:
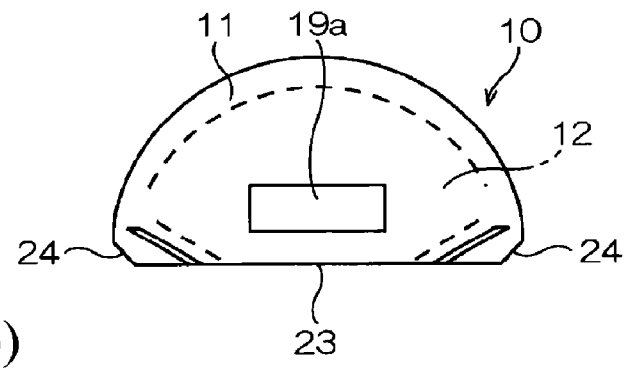
Figure 3:
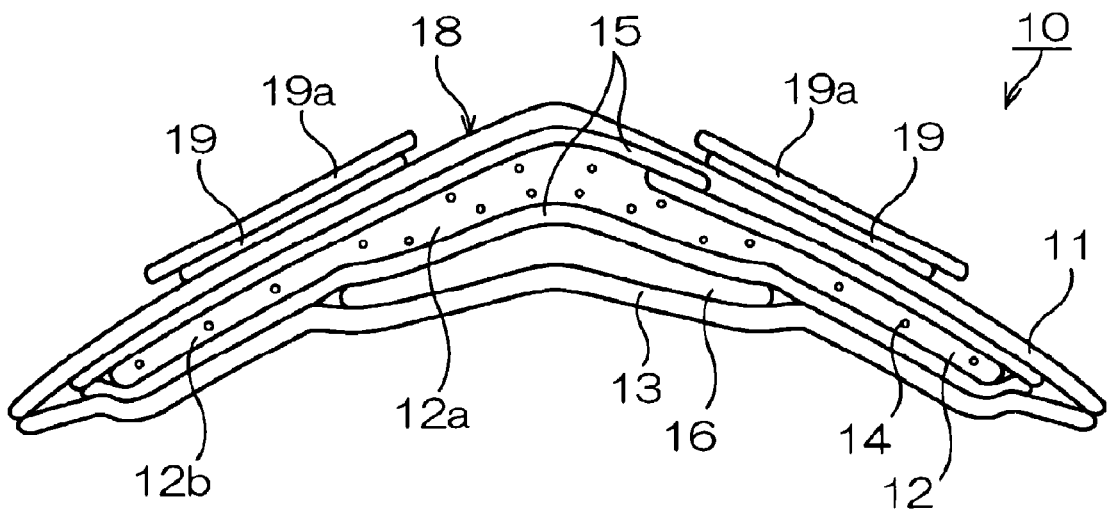
FIG. 3 is a schematic cross-sectional view taken along line A-A of FIG. 1.
Figure 4:
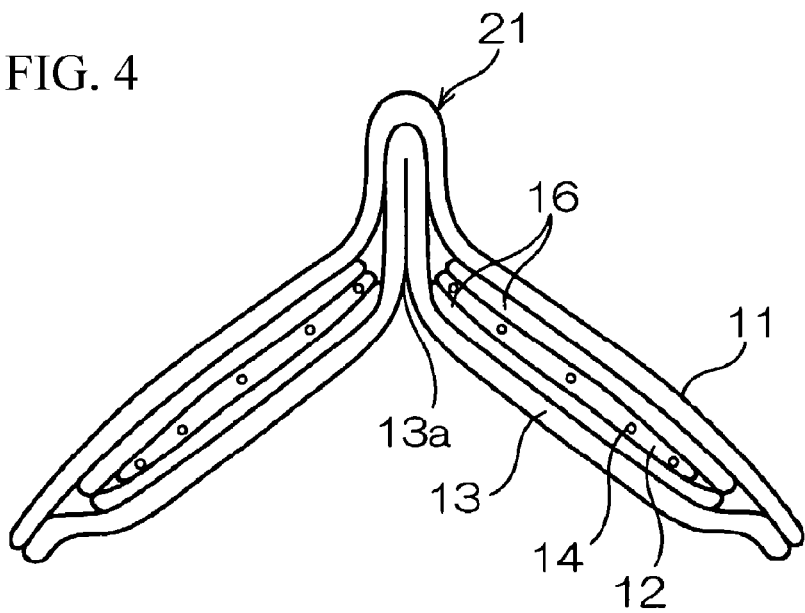
FIG. 4 is a schematic cross-sectional view taken along line B-B of FIG. 1.

FIG. 1 is a schematic perspective view in which an embodiment of a breast-milk pad made in accordance with principles of the presently disclosed subject matter is viewed from the outer side thereof, FIG. 2(a) is a schematic expanded view of the breast-milk pad of FIG. 1, FIG. 2(b) is a schematic view in which the breast-milk pad of FIG. 1 is folded, FIG. 3 is a cross-sectional view taken along line A-A of FIG. 1, and FIG. 4 is a cross-sectional view taken along line B-B of FIG. 1.

The structure of this embodiment of the breast-milk pad will be described with reference to these drawings.

As shown in FIG. 1, FIG. 3 and FIG. 4, back sheet 11 is disposed on the outer side of a breast-milk pad 10 (upper surface side as shown in FIG. 1), and a top sheet 13 is disposed on the inner side (upper surface side as shown in FIG. 1) that comes into contact with the skin of a user when attached.

As shown in FIG. 3 and FIG. 4, an absorber 12 is disposed between the top sheet 13 and the back sheet 11, hence the breast-milk pad 10 is a product the entire shape of which is, for example, a substantially circular shape as shown in FIG. 2(a).

The absorber 12 can be wrapped by tissues 15. Furthermore, the immediate inside of the top sheet 13, which is adjacent the outer side of the absorber 12 wrapped by the tissues 15, is provided with an absorbing/dispersing layer (sub-layer) 16.

For the abovementioned back sheet 11, it is possible to select a somewhat flexible material that does not allow passage of liquid but can allow water vapor to penetrate in order to prevent stuffiness. Also, the back sheet 11 can be formed of a soft material as compared to a conventionally-used back sheet that can be thermally deformed. Such a material, for example, can be polyethylene or other resin film, a sheet material obtained by laminating a nonwoven fabric on the outer side of a polyethylene laminate nonwoven fabric or other resin film, or a melt blown nonwoven fabric can be used, but it is also possible to use a laminate material of a nonwoven fabric and a resin film in terms of obtaining good touch and manufacturability.

The above described top sheet 13 is a member that comes into direct contact with the User's skin, and a nice and soft material that allows good permeation of moisture, such as breast milk, is selected. Specifically, because the top sheet 13 directly touches the user's skin, an appropriate material that does not damage the skin can be selected with a nice, soft feel and the like in mind. In some cases, a dry-mesh sheet (net sheet formed of polyethylene or the like), or a nonwoven fabric formed of a natural fiber such as rayon or of a resin fiber such as polyethylene is used, but it is possible to select a nonwoven fabric having a mixture of a natural fiber and a thermal adhesive fiber in terms of obtaining good touch and manufacturability.

A material having excellent liquid absorbency is selected as the absorber 12, and, for example, a fibriform body, a stacked body or a sheet body made of pulp can be used. Moreover, in the absorber 12, such pulp material is immixed with a granular polymer 14, which is a material having excellent liquid absorbency and functions to hold liquid as is or semi-solidified or solidified liquid.

A water-absorbing polymer, for example, is an appropriate material for configuring the polymer 14, and examples thereof include a polyacrylate copolymer, a hydrolystate of a starch-acrylonitrile graft copolymer, a starch-acrylic acid graft copolymer, a polyvinyl alcohol-acrylate copolymer, a carboxymethyl cellulose and the like.

The absorber 12 is wrapped by tissues 15, as shown in FIG. 3 and FIG. 4. Therefore, the granular polymer and the like are prevented from leaking.

As shown in FIG. 3, the central part of the absorber 12 covered with the tissues 15 is configured as a thick-walled portion 12a having thickness, so as to provide improved cushioning properties and a soft feel to a nipple. Also, an outer peripheral portion of the absorber 12 is configured as a thin-walled portion 12b formed thin, so as to fit over a breast. The thick-walled portion 12a can be formed into a curved surface such that the center thereof is raised upward.

Here, after wrapping the absorber 12 with the tissues 15, the thin-walled portion 12b is compressed more strongly than the thick-walled portion 12a to make a difference in thickness therebetween. Alternatively, the absorber 12 may be formed by stacking the thick-walled portion 12a. Specifically, the absorber for the thin-walled portion 12b having a substantially constant thickness may be formed, and the thick-walled portion 12a may be formed in a substantially central area by disposing, on the thin-walled portion 12b, another layer of the absorber corresponding to the shape of the thick-walled portion 12a.

The absorbing/dispersing layer 16 is disposed in a position corresponding to the nipple at substantially the center of the absorber 12, as shown by a dashed line in FIG. 2(a). Also, because the density of the absorbing/dispersing layer 16 is rougher and/or less than that of the absorber 12, the absorbing/dispersing layer 16 is configured by a material having an increased initial absorption speed of the liquid and excellent dispersibility as compared to the absorber 12, and thus has cushioning properties due to the rough density. In some cases, a bulky nonwoven fabric can be used which includes a fiber having a lower absorbency than the absorber 12, such as polyethylene, polyester or polypropylene with a thickness of approximately 2.2 through 7.7 decitex independently or in combination, or an open-cell foamed sponge can be used, etc. Note that the absorbing/dispersing layer 16 may not only have a square shape but also a rough circular shape, etc.

Also, temporary adhering portions 19, 19 can be temporarily fixed to a brassiere or other underwear worn by the user and may be provided on top and bottom on the outer side of the back sheet 11 of the breast-milk pad 10. The temporary adhering portions 19, 19 are configured by adhering release papers 19a, 19a onto a pressure-sensitive adhesive.

Note that the temporary adhering portion 19 may be disposed in one section or disposed so as to cover the entire outer side of the back sheet 11. In addition, release processing may be performed on an inner surface of a wrapping body 45, which is described hereinafter, without using release papers 19a, 19a.

Furthermore, bonding portions 21, 21 are formed in positions facing each other in the vicinity of the outer edge of the product, or in positions that are symmetric to each other with respect to the center of the circular shape, whereby the entire product is formed into a substantially dome shape having the configuration of an upside down bowl.

The bonding portions 21, 21 are each formed by partially superposing the back sheet 11 and top sheet 13 and bonding the superposed parts of the top sheet opposite to each other.

As shown in FIG. 2(a), which is an expanded view showing a state in which the bonding formed by the bonding portions 21 of the breast-milk pad 10 of FIG. 1 is removed, the absorber 12 at locations corresponding to the sections where the bonding portions 21, 21 should be formed has cutout portions 22, 22 that are formed in positions symmetric to each other at the outer peripheral edge of the circle. The cutout portions 22, 22 gradually narrow down inward, and FIG. 2(b) shows a state in which the breast-milk pad 10 is folded along a folding line 23 connecting inner ends of the respective cutout portions 22, 22 such that the top sheet 13 forms inner surfaces.

In FIG. 2(a), the top sheet 13 is folded into two when the breast-milk pad 10 is bent as shown in FIG. 2(b). Each of the superposed parts of the top sheet 13 that is positioned at each of the cutout portions 22 opposite to the double-fold part is bonded by a top sheet bonding surface 13a, as shown in FIG. 4, whereby each of the bonding portions 21, 21 is formed. The thick-walled portion 12a of the absorber 12 and the absorbing/dispersing layer 16 are not disposed in the section corresponding to each bonding portion 21, and only the top sheet 13 and the back sheet 11 are stacked, hence the bonded state obtained by the top sheet bonding surface 13a can be sustained easily, whereby the formed dome shape can be sustained.

When the breast pad 10 shown in FIG. 2(b) is opened, the entire breast-milk pad 10 forms a substantially dome shape by the bearing power of the bonding portions 21, 21, as shown in FIG. 1.

Moreover, as shown in FIG. 2(b), chamfered portions 24, 24 that have smaller cutouts than the cutout portions 22, 22 are formed in the areas where the back sheet 11 and the top sheet 13 overlap at the inner side of each cutout portions 22, 22 of the absorber 12. Accordingly, the chamfered portions 24, 24 are formed by chamfering the angled portions of the respective bonding portions 21, 21, as shown in FIG. 1.

Figure 5:
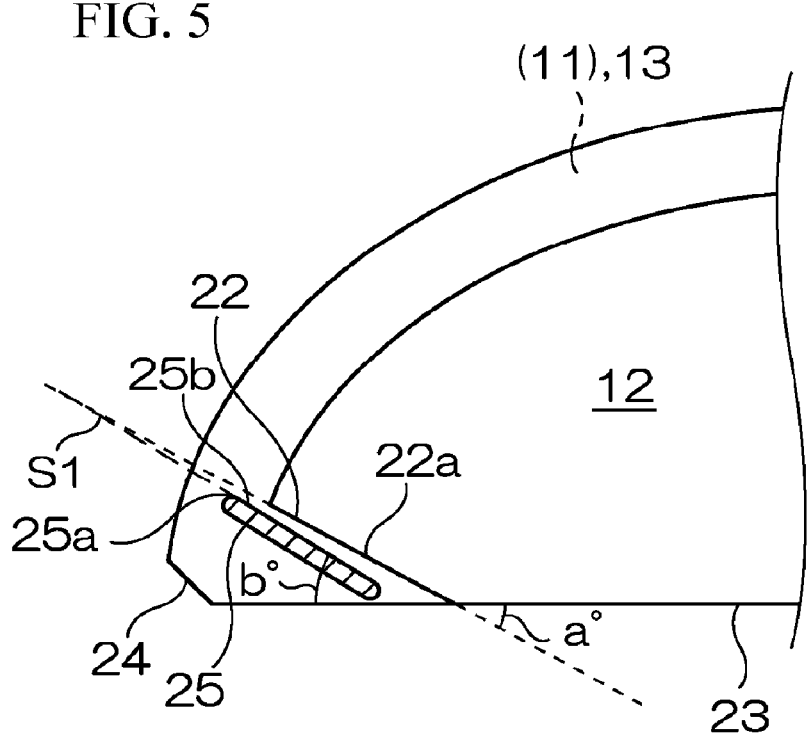
FIG. 5 is an enlarged view showing a sealing structure of the breast-milk pad of FIG. 1.
Figure 6:
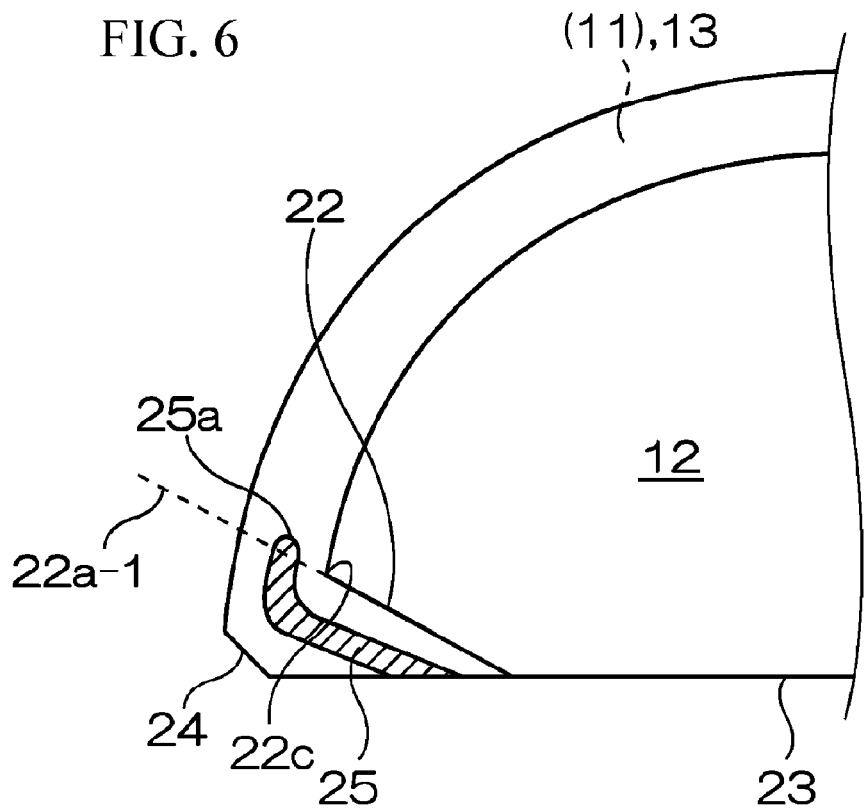
FIG. 6 is an enlarged view showing the sealing structure of the breast-milk pad of FIG. 1.
Figure 7:
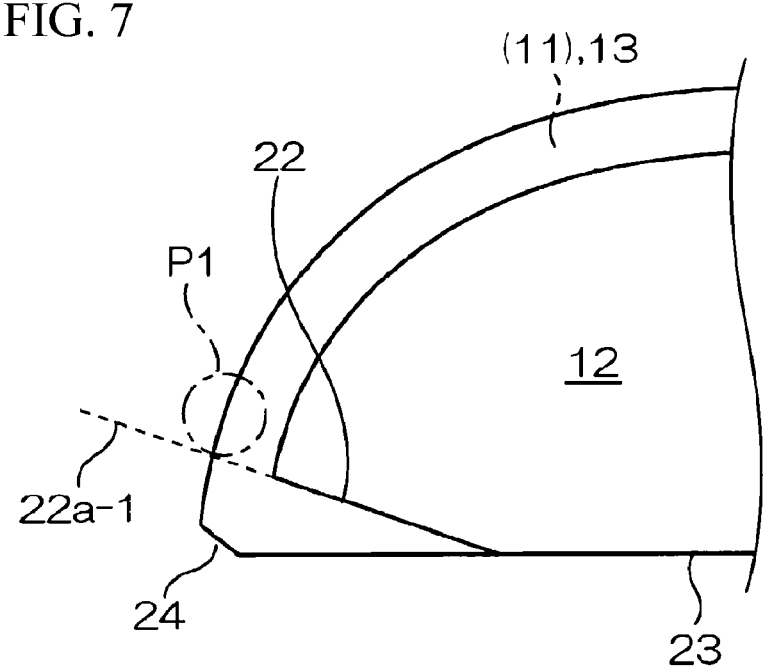
FIG. 7 is an enlarged view showing the sealing structure of the breast-milk pad of FIG. 1.

FIG. 5 through FIG. 7 are each a partial enlarged diagram showing a substantially half area of a detailed configuration of the breast-milk pad 10, that is, a state in which the breast-milk pad is folded into two, as shown in FIG. 2(b).

In FIG. 5, a sealing line 25, which is a heat-sealing portion for heat-sealing and bonding the top sheet 13, is shown with diagonal lines on the inner side of the cutout portions 22 to form the bonding portions 21 described with reference to FIG. 1 through FIG. 4. As described hereinafter, the bonding portion 21 achieves stronger bonding by heat-sealing and bonding the area of the cutout portion 22, and thus forms the sealing line 25 serving as a sealing section.

Here, the sealing line 25 is positioned outside a borderline 22a of the cutout portion 22. Specifically, an angle b formed by an end edge 25b of the sealing line 25 on the borderline 22a side and the folding line 23 is made larger than an intersection angle a of the intersection of the borderline 22a and the folding line 23 illustrated in FIG. 2(a) (b>a). In addition, an outer end 25a of the sealing line 25 can extend beyond the outer edge of the absorber 12 to reach the near side of the outer edge of the breast-milk pad 10.

Figure 9:
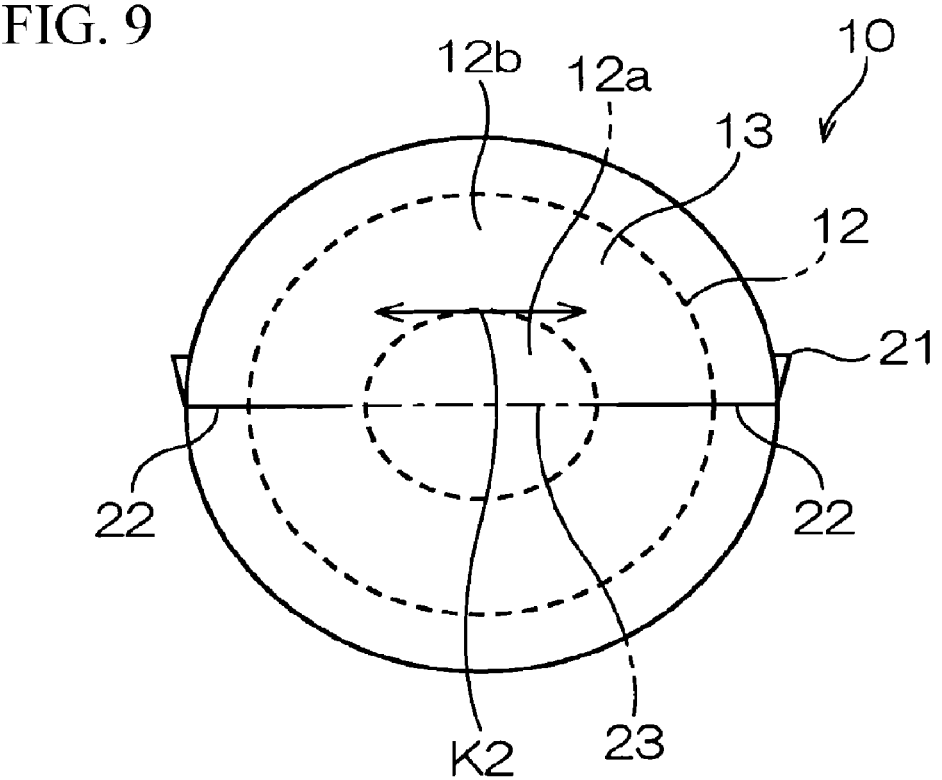
FIG. 9 is a view showing a top sheet side in a state in which the breast-milk pad is opened and used.

Accordingly, the extended line of the end edge 25b of the sealing line 25 and the extended line of the borderline 22a of the cutout portion 22 of the absorber are disposed so as to intersect at an intersecting point SI, whereby the sealing line 25 is disposed such that the outer end 25a is placed proximate to the absorber 12, the cutout portion 22 is narrower at the outer side thereof than the center side. Then, after bonding, when the breast-milk pad 10 is opened as shown in FIG. 9 showing the top sheet 13 in the use state, the cutout portion 22 without the absorber 12 is not present or exposed in the dome-shaped breast-milk pad 10 so that a section that is not capable of absorbing and/or retaining liquid is not present or exposed. Furthermore, because the cutout portion 22 without the absorber 12 is not exposed, a soft feel can be provided to the breast.

Also, in FIG. 6, even if/when the end edge 25b of the sealing line 25 is located slightly away from the borderline 22a, the outer end portion 25a can be caused to extend slightly toward the absorber side beyond an extended line 22a-1 of the borderline 22a of the absorber 12, whereby when it is bonded it includes the extended part. Accordingly, when the breast-milk pad 10 is opened as shown in FIG. 9, the overlap space of the bonding portion is large in the vicinity of the cutout portion 22 so that the borderline 22a of the cutout portion is not exposed by that much.

Note that when the sealing line is formed at the position of an end portion 22c of the borderline 22a of the cutout portion such as to extend inward from the outer periphery, bonding can be performed securely and a gap corresponding to the abovementioned gap size S1 cannot be noticed.

Furthermore, in order to create a further curved dome, the borderline 22a of the cutout portion 22 can be formed into a curve line bulging toward the folding line 23, and the sealing line 25 can also be formed into a parallel curve line. Accordingly, the shape of the curved surface of the opened breast-milk pad 10 and the shape of the curved surface of the borderline 22a of the bonding portion 21 form substantially the same curved surface, as shown in FIG. 1.

In addition, when overlapping the top sheet 13 and the back sheet 11 and bonding the opposing parts of the top sheet 13 together, it is possible to eliminate, from the heat-sealing portion or sealing line, an outer edge portion PI positioned on the outermost side of the absorber (upper part in FIG. 7) and near the extended line 22a-1 of the borderline 22a of the absorber 12, as shown in FIG. 7, so that the outer edge portion P1 is not bonded.

Accordingly, the outer edge portion shown by reference numeral P1, which corresponds to the outer edge of the breast-milk pad 10 shown in FIG. 1, can be prevented from rising and providing uncomfortable sensation to the user's skin.

Figure 8:
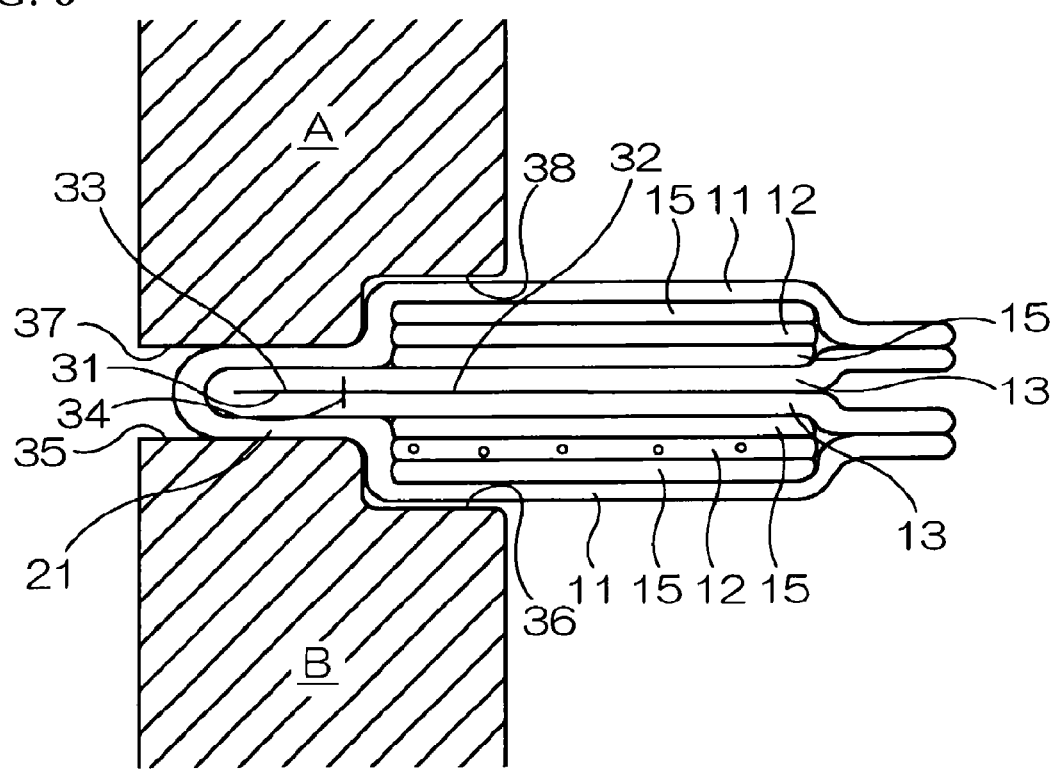
FIG. 8 is an enlarged view showing the sealing structure of the breast-milk pad of FIG. 1.

FIG. 8 shows another technique of forming the bonding portions, the technique here being a fusing method.

FIG. 8 is a partial enlarged view in which a heat sealer having heating devices A and B is used for folding the breast-milk pad 10 into two as shown in FIG. 2(b) and bonding the bonding portions 21.

With a boundary portion 34 as a boundary, the bonding portion 21 is inserted into a strong fusing portion 33 formed between a lower surface 37 of the narrowed heating device A and an upper surface 35 of the heating device B in relation to the cutout portion 22 where only the top sheet 13 and the back sheet 11 are overlapped. At the same time, a thick area in which the absorber positioned on a farther side is inserted into a weak fusing portion 32 which is formed in a wide area between a lower step portion 38 of the heating device A and an upper step portion 36 of the heating device B, and then heated/pressed.

Consequently, the pressed bonding portion 21 of the cutout portion 22 where only the top sheet 13 and the back sheet 11 are overlapped is covered with an area heat-sealed by the weak fusing portion 32 such that the absorber 12 is interposed in the area, whereby the breast-milk pad 10 is prevented from providing uncomfortable sensation to the user's skin, and the occurrence of breakage or other damage to the material of the outer edge portion which is caused by pressing the bonding portion more than necessary can also be prevented.

Note here that the weak fusing portion 32 is formed by interposing and heat sealing the absorber 12, but only the strong fusing portion 33 may be formed by forming the sealing line 25 as shown in FIG. 5 or FIG. 6, or the weak fusing portion 32 and the strong fusing portion 33 may be combined.

Moreover, although the top sheet 13 is heat-sealed, the bonding portion 21 may be formed by using a hot-melt adhesive or other adhesive, and heat-sealing and adhesive may be combined and used such that, for example, heat-sealing is used at the position contacting the body and the adhesive is used at the position that does not contact the body.

FIG. 9 is a view showing the top sheet in a state in which the breast-milk pad 10 is opened and used, and is also a view describing the direction of orientations of the fibers of a nonwoven fabric used for forming the top sheet 13. In the top sheet 13 of the breast-milk pad 10, the fibers configuring the top sheet 13 can be oriented in an aligned manner along a direction K2 in which the folding line 23 of the breast-milk pad 10 extends.

Accordingly, when the product is attached such that the direction in which the folding line 23 extends is oriented in the vertical direction, the orientations of the fibers are set in a direction perpendicular to the vertical direction of the body, whereby the breast milk is prevented from leaking particularly in a downward direction along the orientations of the fibers.

In addition, the thick-walled portion 12a having a substantially round shape, shown by a dashed line, is formed in a substantially central area of the absorber 12 shown by a dashed line, the substantially central area being the inner side of the cutout portions 22, 22 that are bonded by the bonding portions 21 and deformed so as not to be exposed to the body side.

Figure 10:
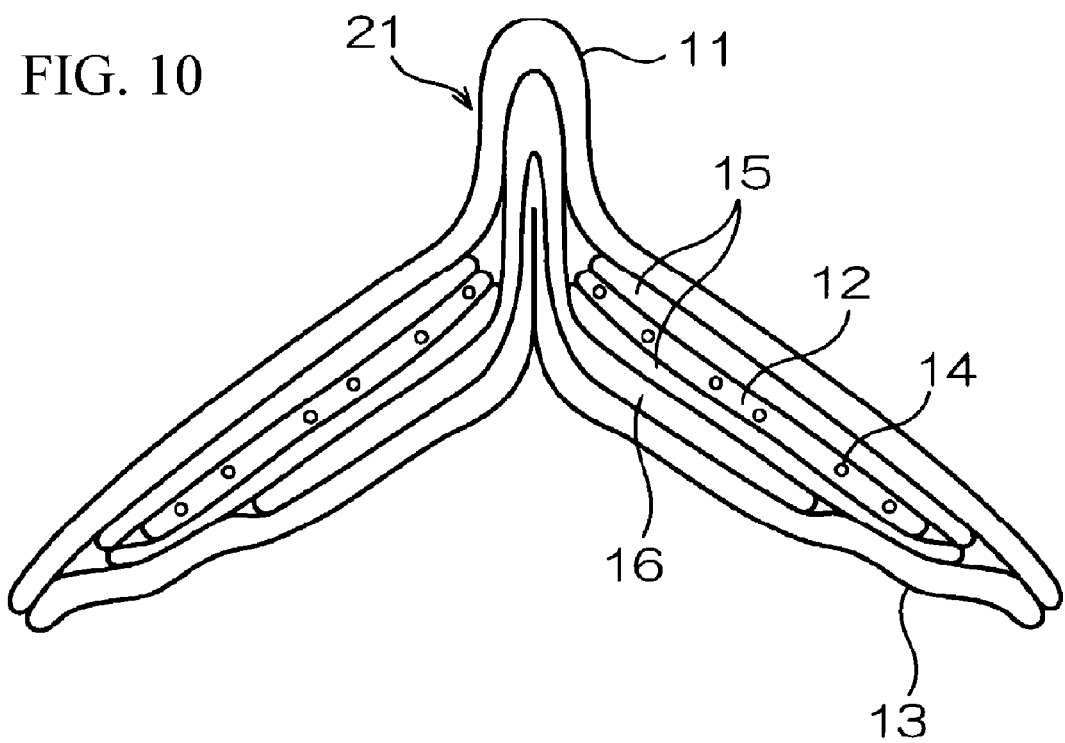
FIG. 10 is a schematic cross-sectional view showing the structure of a modification of a breast-milk pad.

FIG. 10 shows a modification of a part shown in FIG. 4, that is, the cross-sectional view taken along line B-B of FIG. 1.

When the absorbing/dispersing layer 16 is interposed in the bonding portion 21 as shown in FIG. 10, a cushion layer becomes present as the absorbing/dispersing layer 16 in the cutout portion 22 of the absorber 12, hence good touch to the user's skin can be obtained and comfort can be improved.

The present embodiment is configured as described above, wherein each of the bonding portions 21, 21 of the breast-milk pad 10 is obtained by overlapping the top sheet 13 and the back sheet 11 and bonding the opposing parts of the top sheet 13 together at the bonding surface 13a within the cutout portion 22 of the absorber 12, and the absorber 12 is hardly bonded.

Specifically, since the thick absorber 12 is not overlapped or bonded together, the breast-milk pad can be produced relatively easily and the bonding can be prevented from being removed. Moreover, the dome shape is not created by bonding the absorber 12 together, hence even when the absorber 12 is substantially flattened when the absorber 12 absorbs liquid during use, the bonding that is formed between the top sheets at the bonding portions 21, 21 supporting the dome shape does not change. For this reason, the dome shape is prevented from being extremely unbalanced and the fitting properties are prevented from being damaged.

Furthermore, because the gatherings are not provided in the section abutting on the skin surface of the user, and the section hardened by heat does not contact the skin surface, uncomfortable sensation is extremely small. In addition, because those gatherings used in the conventional techniques are not used to form the dome shape, it is not necessary to use an elastic body such as rubber in the interior, hence the production of the breast-milk pad becomes simple.

Particularly, when creating the bonding portions 21, the top sheet 13 can include the thermal fusion material so that when the breast-milk pad 10 is folded as shown in FIG. 2(b), the bonding portion is heated from the back sheet 11 side and the top sheet 13 is fused, whereby the bonding portion 21 is formed. Accordingly, the bonding portion supporting the dome shape can be created only in the heat sealing process. Also, since an adhesive is not used for bonding, no foreign-body feeling is generated by an adhesive interposed at a predetermined volume.

When the bonding portion 21 is chamfered to provide the chamfered portion 24 as shown in FIG. 1, even when the angled portion abuts on the inner surface of underwear such as a brassiere and folded back to the body side when the breast-milk pad 10 is attached to the inner side of the underwear as described hereinafter, it does not cause an uncomfortable sensation.

Note here that although only the substantially angled portion of the chamfered portion 24 is cut, it may be cut to obtain a larger chamfer as long as the bonding portion 21 can be bonded securely, and the chamfered portion 24 may be formed by cutting the bonding portion 21 into a number of pieces.

In addition, the present embodiment is configured such that the folding line 23 serves as a guide along which the product is folded into two, as shown in FIG. 2(*a*).

Therefore, as described hereinafter, the breast-milk pad 10 is folded into two in flat and made compact by reducing the thickness thereof when storing the breast-milk pad 10 in a packaging or wrapping. But the dome shape can be realized without damaging the structure supporting the dome shape in most or all storing or packaging devices and achieved simply by opening the double-fold part when the user uses the breast-milk pad 10, hence it can be used simply.

FIG. 11 is a schematic perspective view showing a second embodiment.

In the embodiment shown in FIG. 2 the sections with the same reference numerals as those of the breast-milk pad of FIG. 1 are configured in the same way, hence their overlapping explanations are omitted and the differences are mainly described hereinafter.

In a breast-milk pad 10-1, the top sheet 13 and back sheet 11 serving as laminate materials and/or outer edge cut portions 41, 41 obtained by removing the absorber are formed in an outer edge portion of the breast-milk pad 10-1. The outer edge cut portions 41 are each formed into a diagonal straight line or inwardly convex curve line by cutting an upper curved part that is convex outward on the circular product.

Accordingly, when, for example, the breast-milk pad 10-1 is stored in a cut portion BC of a brassiere B as shown in FIG. 12, the outer edge cut portion 41 of the breast-milk pad 10-1 is positioned in the vicinity of an upper edge of the cup portion BC so that the outer edge cut portion 41 is completely hidden inside the cup portion BC. Therefore, it is difficult to tell whether the breast-milk pad 10-1 is attached because the breast-milk pad 10-1 is not exposed from the cup portion BC, and the breast-milk pad 10-1 can be used integrally with the brassiere B so as to alleviate discomfort. Note here that each of the outer edge cut portion 41, 41 is formed in two sections but may be conformed to the shape of the right or left cup so as to serve as an inner part corresponding to the cup.

Figure 13:
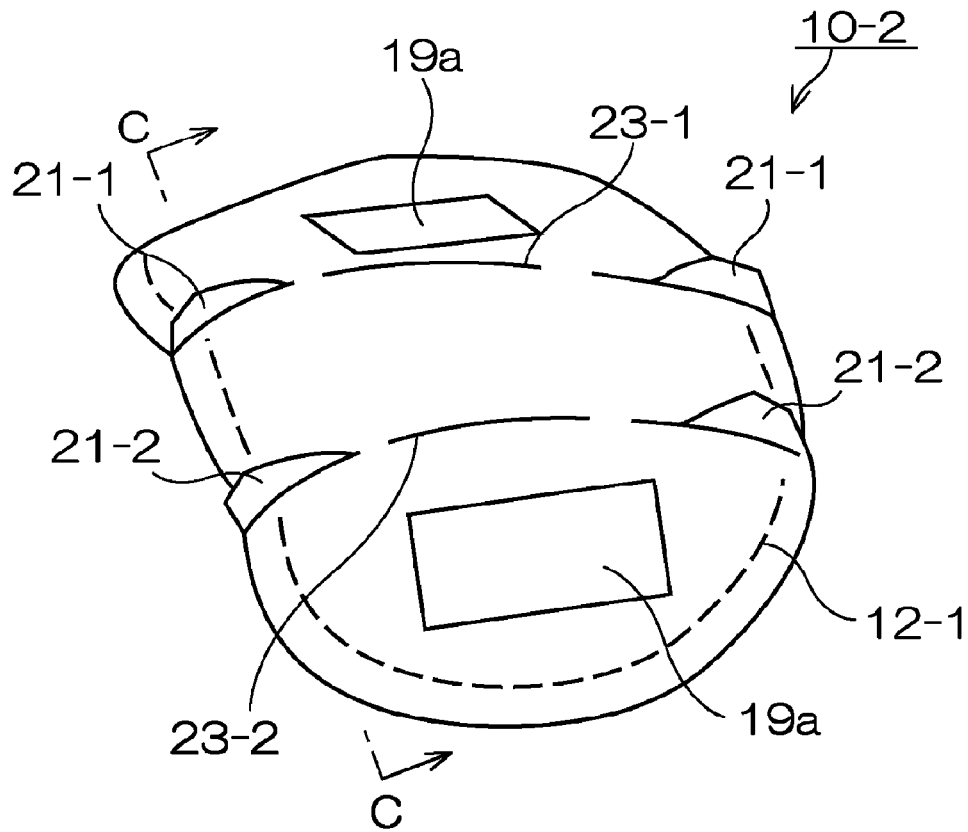
FIG. 13 is a schematic perspective view of a third embodiment of a breast-milk pad of the presently disclosed subject matter.
Figure 14:
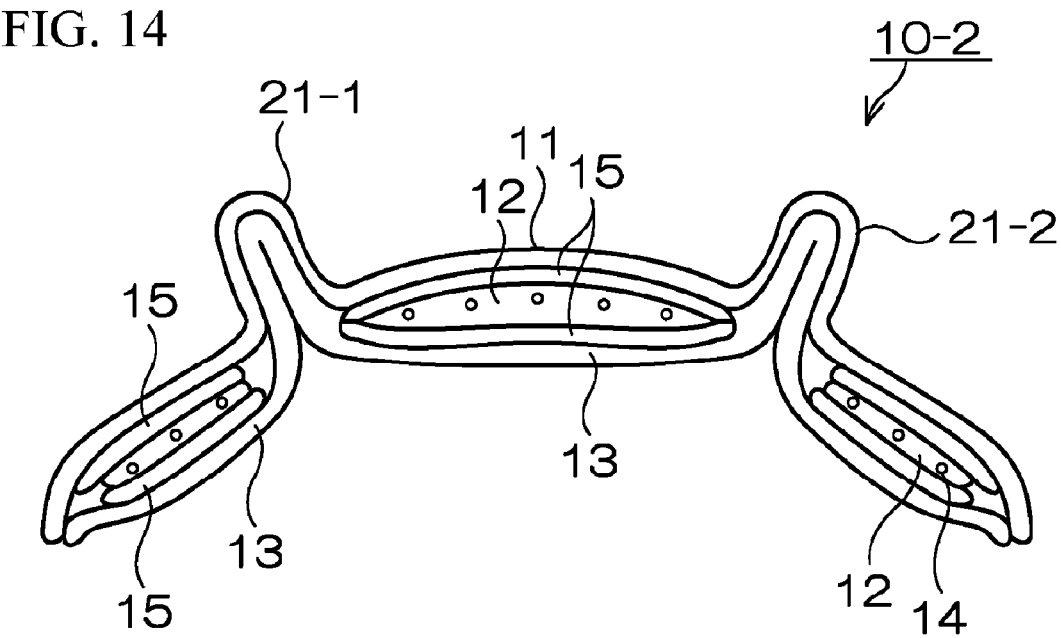
FIG. 14 is a schematic cross-sectional view taken along line C-C of FIG. 13.
Figure 15:
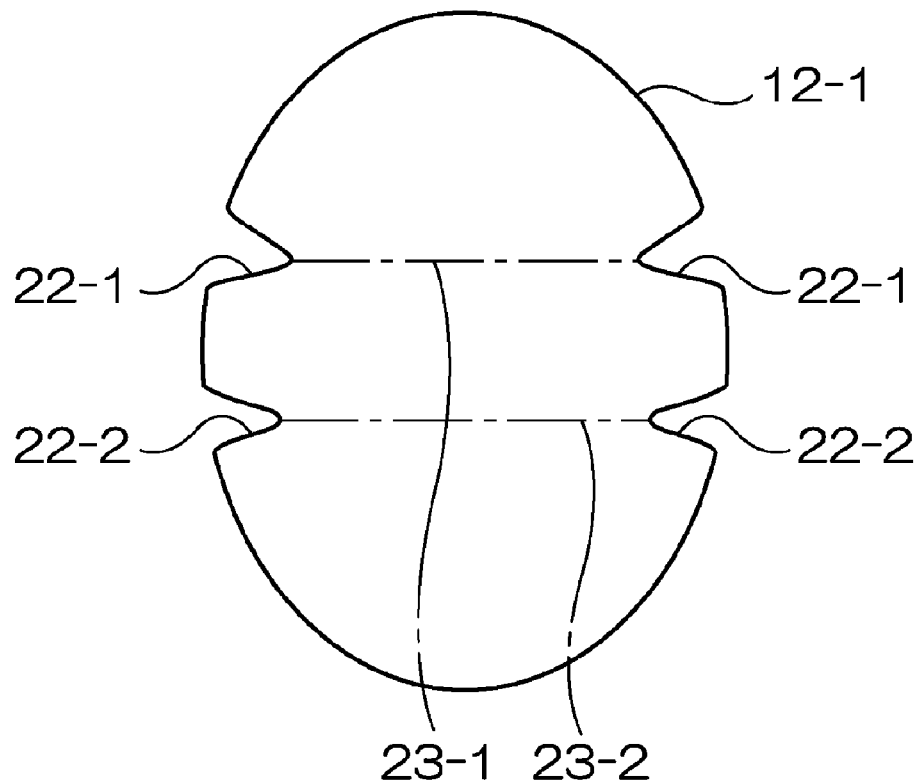
FIG. 15 is a schematic expanded view of an absorber of the breast-milk pad of FIG. 13.
Figure 16:
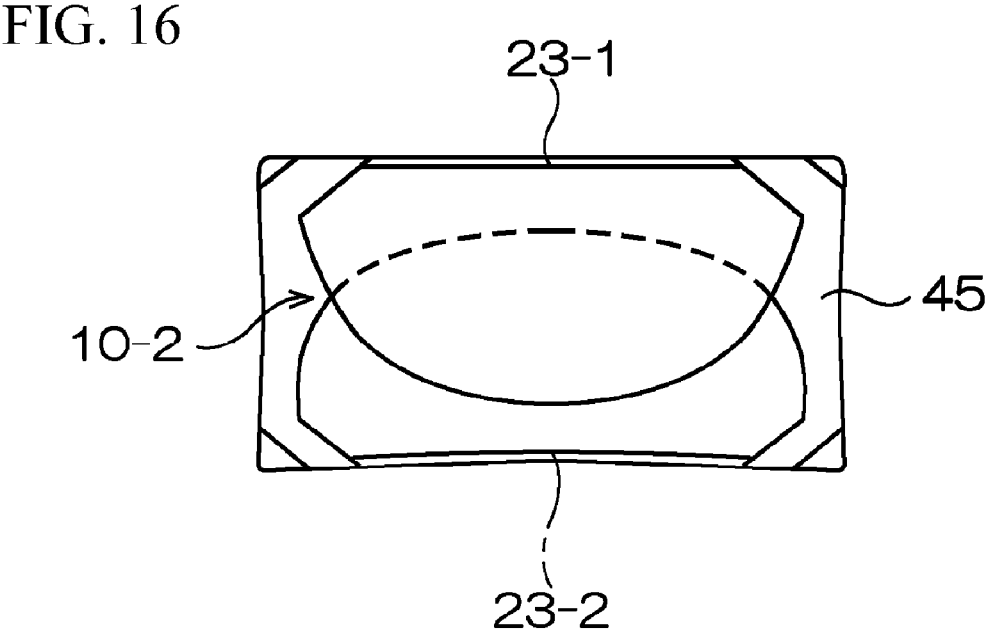
FIG. 16 is a view in which the breast-milk pad of FIG. 13 is folded into three.

FIG. 13 through FIG. 16 each show a third embodiment of the breast-milk pad, FIG. 13 being a schematic perspective view of the breast-milk pad, FIG. 14 being a schematic cross-sectional view taken along line C-C of FIG. 13, FIG. 15 being a schematic expanded view of the absorber of the breast-milk pad, and FIG. 16 being a schematic plan view showing a state in which the breast-milk pad is folded up and stored in the wrapping body.

In FIG. 13 through FIG. 16, the sections with the same reference numerals as those of the breast-milk pad of FIG. 1 are configured in the same way, hence their overlapping explanations are omitted and the differences are mainly described hereinafter.

As shown in FIG. 13, in a breast-milk pad 10-2 two folding lines 23-1, 23-2 are formed so as to correspond to, for example, positions for sectioning the dimension of one of the directions of the breast-milk pad 10-2 into three parts.

The structure in which first bonding portions 21-1, 21-1 and second bonding portions 21-2, 21-2 are formed in the vicinity of both outer edges of the product along the folding lines 23-1, 23-2, respectively, is the same as the structure of the first embodiment.

As shown in FIG. 15, an absorber 12-1 within the stacked body has first cutout portions 22-1, 22-1 and second cutout portions 22-2, 22-2.

The first cutout portions 22-1, 22-1 are connected to each other so that the first folding line 23-1 is provided, and the second cutout portions 22-2, 22-2 are connected to each other so that the second folding line 23-2 is provided. By stacking the absorber 22-1 and bonding the bonding surfaces 13*a* of the top sheet 13 together at the bonding portions 21-1, 21-2, a substantially dome shape is formed in which two folding points (folding lines) are provided at the positions of the bonding portions 21-1, 21-2 so as to be positioned at the top and bottom of the nipple respectively, as shown in FIG. 14.

FIG. 16 shows the first folding line 23-1 and the second folding line 23-2, wherein, as described with reference to FIG. 2, the top sheet is folded inward and stored in the transparent wrapping body 45, for example.

In this manner, in the breast-milk pad 10-2 of the third embodiment, the cutout portions are formed at four sections facing each other at the outer edge portion of the absorber to obtain two pairs of cutout portions, hence, by folding the breast-milk pad along the folding lines 23-1, 23-2 connecting the respective pairs of cutout portions facing each other, the entire product is folded into three. Accordingly, as shown in FIG. 16, the breast-milk pad 10-2 can be stored further compactly, the folding points are disposed so as to have the nipple therebetween and so that the breast-milk pad 10-2 can contact the nipple planarly, the relatively smooth curved surface is formed by the two top and bottom sections, and the dome shape can be securely formed due to an increase in the number of bonding portions, whereby the shape of the breast-milk pad 10-2 can be maintained.

Note here that although the four cutout portions are formed, the dome shape may be formed by six, eight or more even-numbered cutout portions and have corresponding bonding portions or folding lines. Furthermore, the upper first cutout portion 22-1 may be cut out more deeply (longer) than the lower second cutout portion 22-2 or cut out so as to have a narrower width than the second cutout portion 22-2. The thus obtained first and second cutout portions 22-1, 22-2 may be bonded to the bonding portions 21-1, 21-2 respectively, whereby the lower bonding portion 21-2 forms a deep dome shape, which is close to the shape of the nipple.

(Method for Producing the Breast-milk Pad)

Next, embodiments of the method for producing the breast-milk pad are described.

A manufacturing apparatus, not shown, can include a conveyor line serving as a conveyor or other conveying means, and a manufacturing process proceeds in a direction of an arrow K1 along this conveyor line.

(Molding Process)

Figure 17:
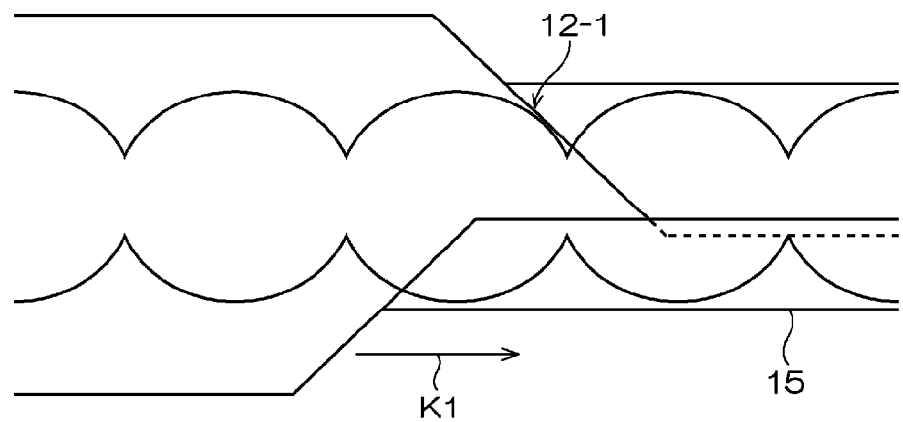
FIG. 17 is a view showing a process for the absorber that is performed in a process of producing the breast-milk pad of FIG. 1.

In FIG. 17, first the tissue 15 is fed out as a belt-like material from a supply roll, not shown, at the first part of the conveyor line. The tissue 15 is sent in the direction of the arrow K1 along the abovementioned conveyor line. Then, the absorber 12-1, which is obtained by mixing crushed pulp fed from an unshown pulp supply means with a polymer and molding the thus obtained mixture, is disposed in the center of the tissue 15 on the conveyor line. The tissue 15 is then folded back inward by a folding board, and the absorber 12 made of pulp and the like is wrapped by the tissue 15 to form an absorber main body. At this moment, the absorber, not shown, is configured such that adjacent circular absorbers for the respective products are partially connected to each other such as to form an entirely long consecutive absorber (called "continuous absorber 12-1" hereinafter).

Figure 18:
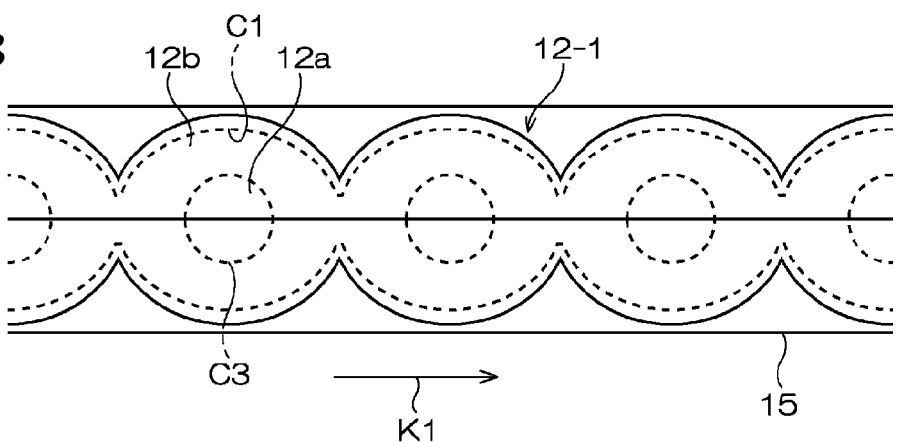
FIG. 18 is a view showing a process for the absorber that is performed in a process of producing the breast-milk pad of FIG. 1.

Next, in order to form the continuous absorber 12-1 wrapped by the tissue 15 into a substantially circular continuous body again, the outline of the absorber 12-1 is cut along with the tissue along a dashed line C1 so as to correspond to the shape and size of the circle of each product, as shown in FIG. 18.

At this moment, the absorber 12 is subjected to embossing C3 from the top and bottom thereof so that the pressure of the peripheral portion of the absorber 12 is higher than that of the central portion, and then the absorber 12 is compressed so that the central portion forms the thick-walled portion 12a and the outer peripheral portion forms the thin-walled portion 12b. Then, the tissue 15 and the absorber 12-1 are securely integrated. Note that the thickness of the absorber 12-1 may be made even and a small absorber corresponding to the thick-walled portion 12a may be superposed thereon.

Figure 19:
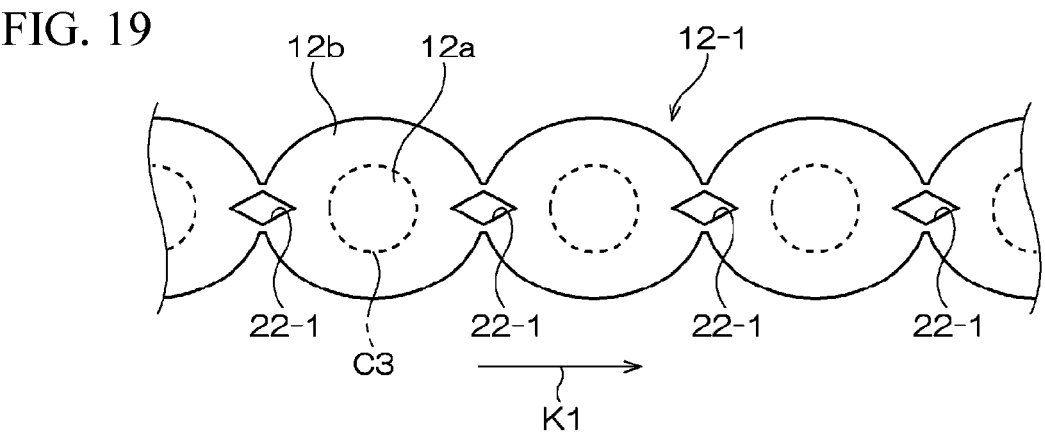
FIG. 19 is a view showing a process for the absorber that is performed in a process of producing the breast-milk pad of FIG. 1.

Next, as shown in FIG. 19, a punched portion 22-1 is obtained by die-cutting a boundary section having the size of each product unit of the continuous absorber 12-1 wrapped by the tissue 15. At this moment, the generated chads are securely suctioned and discarded so that the polymer or pulp does not remain at the punched portion. Moreover, as is understood from the drawing, the punched portion 22-1 has a substantially diamond shape in which the two cutout portions 22 described in FIG. 2(a) are integrated at the wide parts thereof, hence, in the absorber of each product unit, the cutout portions are punched such that the cutout width of each cutout portion gradually narrows down inward.

Figure 20:
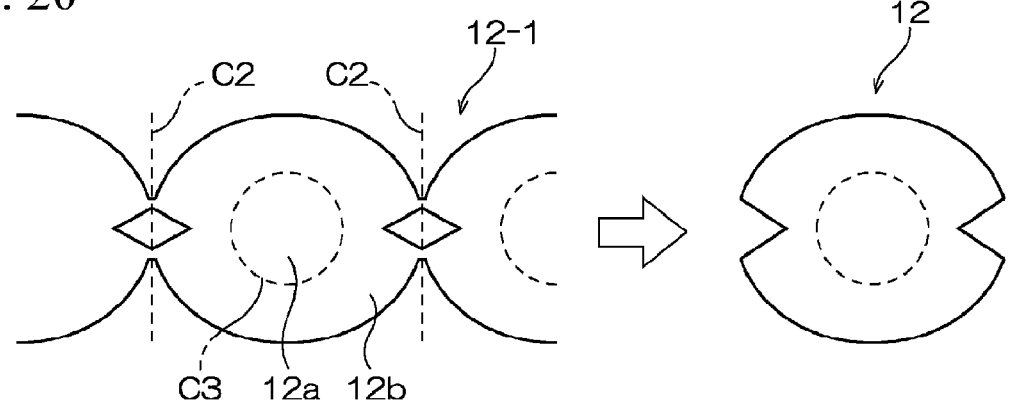
FIG. 20 is a view showing a process for the absorber that is performed in a process of producing the breast-milk pad of FIG. 1.

Specifically, as shown in FIG. 20, the continuous absorber 12-1 is cut by a mat cutter, at the position of a cutting section C2 corresponding to each product, whereby the absorber 12 is obtained. At this moment, the absorber 12 is subjected to embossing C3 from the top and bottom thereof so that the pressure of the peripheral portion of the absorber 12 is higher than that of the central portion, and then the absorber 12 is compressed so that the central portion forms the thick-walled portion 12a and the outer peripheral portion forms the thin-walled portion 12b. Specifically, in an embossing machine for embossing the absorber 12, a projection corresponding to the thin-walled portion is formed in the upper part side of the absorber 12-1, while the section corresponding to the thick-walled portion 12a is depressed, and the lower part side of the absorber 12-1 is formed flat. This absorber 12 wrapped by the tissue is held between the top sheet and the back sheet and stored in a subsequent process. Note that when the thin-walled portion 12b is formed by this embossing C3, a projection higher than that for forming the thin-walled portion 12b around an outer periphery of the embossing C3 may be formed on the embossing machine so that a circular groove deeper than the thin-walled portion 12b can be embossed along the outer periphery of the thick-walled portion 12a.

Note here that the absorber 12 is wrapped by the tissue 15. Alternatively, two tissues 15 may be used on top and bottom of the absorber 12 to hold the absorber 12 therebetween.

Furthermore, the absorber 12 is formed by cutting the continuous absorber 12-1. However, a suction pattern drum or the like in which the cutout portion 22 is patterned in concave shape may be used to form and dispose the absorber which has the cutout portion 22 molded thereon beforehand onto the tissue 15. Also, the absorber may be formed and directly disposed on the top sheet 13 without using the tissue 15 described hereinafter, or, instead of embossing and forming the thick-walled portion 12a and the thin-walled portion 12b, the suction pattern drum or the like may be used to mold the absorber 12 three-dimensionally, or the absorber 12 may be formed in the form of a double layer at the thin-walled portion 12a.

Figure 21:
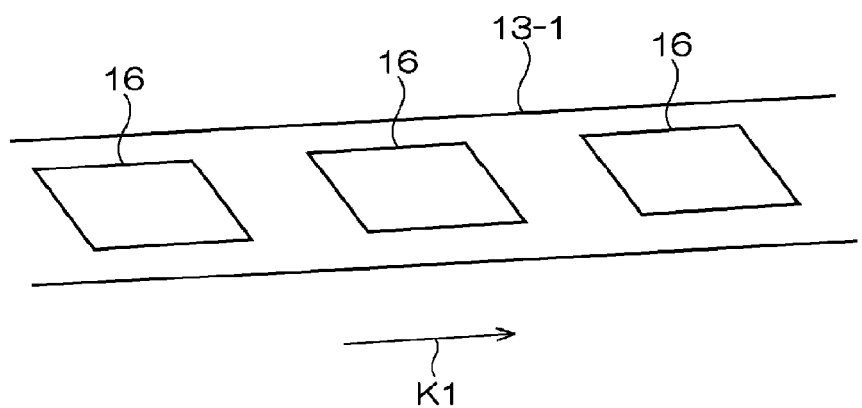
FIG. 21 is a view showing a process for the top sheet that is performed in a process of producing the breast-milk pad of FIG. 1.

FIG. 21 shows a belt-like material 13-1 for forming the top sheet 13, which is a surface material. In the manufacturing process, the belt-like material 13-1, which is formed from a dry-mesh sheet that is a net sheet formed of polyethylene or the like, or a nonwoven fabric formed of a natural fiber such as rayon or of a resin fiber such as polyethylene, e.g., a nonwoven fabric in which a thermal adhesive fiber is mixed, is fed from the supply roll and conveyed along the conveyance direction K1.

A rubber-based or olefin-based hot-melt adhesive or other adhesive (fixing HM) is applied onto the belt-like member 13-1. Then a sub-layer 16 serving as a square or rectangular absorbing/dispersing layer is disposed thereon in sequence at intervals corresponding to the products. The sub-layer 16 is then adhered to the belt-like material 13-1 and conveyed integrally.

Figure 22:
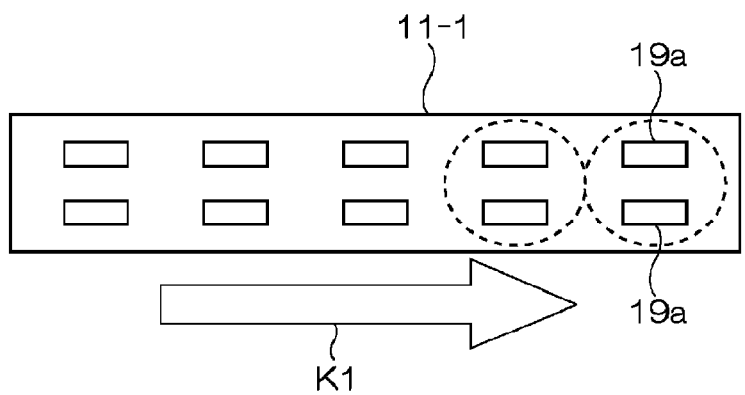
FIG. 22 is a view showing a process for a back sheet that is performed in a process of producing the breast-milk pad of FIG. 1.

FIG. 22 shows a state in which, in order to form the back sheet 11, a continuous belt-like material 11-1 formed from a nonwoven fabric and a laminate material of a resin film is supplied from the supply roll, not shown, and sent in the conveyance direction K1, the nonwoven fabric being, for example, a polyethylene or other resin film, a sheet material obtained by laminating a nonwoven fabric on the outer side of a polyethylene laminate nonwoven fabric or other resin film, or a melt blown nonwoven fabric, etc.

A pressure-sensitive adhesive for preventing displacement is applied to each of the release surfaces of two release papers 19a by hot-melt coating, and pairs of the release papers 19a are attached at regular intervals onto the belt-like material 11-1 sectioned into two in the width direction, whereby the pressure-sensitive adhesive is applied to the back sheet 11. Areas shown by the dashed lines in a latter stage are the areas that are cut into each product unit.

(Stacking Process and Sealing Process)

The abovementioned absorber 12 shown in FIG. 20 is held between the belt-like member 13-1 of the top sheet shown in FIG. 21 and the belt-like member 11-1 of the back sheet to which the adhesive is applied beforehand, to stack and fix the belt-like member 11-1 of the back sheet and the absorber 12 together, and the belt-like member 11-1 of the back sheet and the belt-like member 13-1 of the top sheet are also adhered and fixed in the outer peripheral area of the absorber 12 and the cutout portion 22, whereby the absorber 12 is fixed while being held between the top sheet 11 and the back sheet 13. In this stacked state a single continuous belt-like material 10-5 (FIG. 23) is configured. Note that so-called pin-embossing may be performed to overlap the belt-like member 13-1 of the top sheet and the absorber 12 together beforehand and the fibers of the belt-like member 13-1 and of the absorber are entwined while forming an opening by means of a number of tiny needles from the top sheet 13 side, to fix the belt-like member 13-1 and the absorber 12.

Reference numeral 10 shown by a dashed line indicates an area constituted finally by the breast-milk pad 10, which is the product. The belt-like member 13-1 of the top sheet has the thermal fusion material, and is thereby heated/pressed from the belt-like member 11-1 of the back sheet side so that the belt-like member 13-1 is heat-sealed along the outer periphery of the breast-milk pad 10 that is shown by the dashed line. Here, the thermal fusion material is, for example, a polyolefin-based fiber material such as polyethylene or a fibrous material obtained by combining polyethylene with polypropylene, or polyethylene with polyester or the like, or combining a plurality of resins, etc.

(Folding Process)

Next, as shown in FIG. 23, the belt-like material 10-5 is folded into two along the folding line 23 connecting the cutout portions 22, i.e., the folding line 23 described with reference to FIG. 2, by means of the folding board, which is material folding means provided in the manufacturing process, with the belt-like member 13-1 of the top sheet inside. Note that prior to the folding process which is performed using the folding board, a compressing process can be executed for forming a folding habit following the folding line 23 to the absorber 12-1, whereby a gentle groove is formed by compressing the absorber 12-1 linearly by means of a rotating disk or the like so that the belt-like material 10-5 can be easily folded into two along this groove.

Moreover, not only the folding board but also a board-like folding machine that rotates or moves vertically may be used after cutting into product units, to fold the breast-milk pad 10 into two.

(Bonding Process)

Next, a side sealing process is executed subsequent to the process shown in FIG. 24 and FIG. 25, whereby the bonding portions 21 described with reference to FIG. 2 are formed.

Specifically, in the belt-like member 10-5 shown in FIG. 24, the area shown by a number of thin parallel lines Hi is a section that is heated/pressed from the top and bottom thereof by a roll-like heat sealer or the like, and most of this area is cut/discarded later and temporarily joined so that the folded belt-like material 10-5 is not opened in a subsequent cutting process or the like. Therefore, an area other than the breast-milk pad 10 is temporarily joined and welded without bonding the outer peripheral portion of the breast-milk pad 10.

In addition, the area shown by reference numeral H2 at each end portion of each breast-milk pad 10 is a first side sealing portion, which is the same as the sealing line 25 serving as a heat sealing portion when heat-sealing and bonding the belt-like material 13-1 of the top sheet on the inner side of the cutout portions 22 when forming the bonding portions 21 described with reference to FIG. 1 through FIG. 4. Since this sealing line 25 was described in detail with reference to FIG. 5 and FIG. 6, the overlapping explanation thereof is omitted. Note here that the first side sealing portion is the same as the sealing line 25 described with reference to FIG. 6.

The areas shown by the parallel lines Hi and reference numeral H2 can be heated/pressed by heat sealing simultaneously by providing a step on a surface against which the heat sealer abuts, and is performed several times or for example three times particularly on the area shown by reference numeral H2 in order to ensure security. Note that the parallel lines Hi and the sealing line 25 of reference numeral H2 may be heated/pressed simultaneously and formed at once.

Furthermore, as shown in FIG. 25, the area shown by reference numeral H3 at each end portion of each breast-milk pad 10 can be bonded. This section is a second side sealing portion to be bonded securely.

Specifically, as shown in FIG. 25, the heat sealer forms the second side sealing portion H3 which is sealed in a direction different from that of the sealing line 25 (area H2) shown in FIG. 24. This second side sealing portion H3 is an additional sealing line, which is superposed and heat-sealed in a direction intersecting with the bent short-side end portion of the sealing line 25 extending along the outer edge of the breast-milk pad 10 (a direction substantially parallel to the folding line 23). The second side sealing portion H3 can function as a sealing portion for preventing the bonding portions 21 from being damaged when the breast-milk pad is opened securely.

(Cutting Process)

Figure 26:
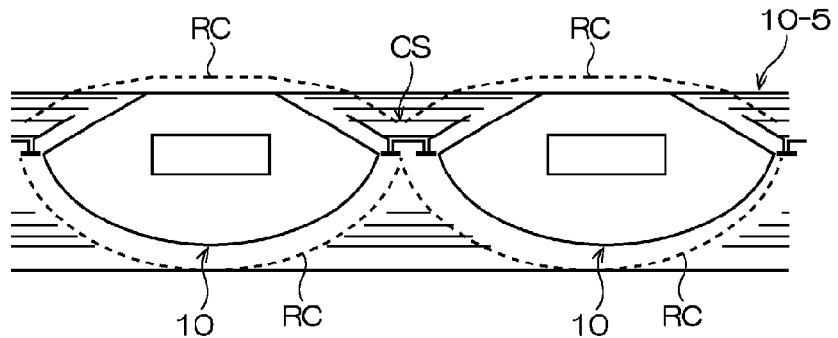
FIG. 26 is view showing a cutting process that is performed in a process of producing the breast-milk pad of FIG. 1.

Next, as shown in FIG. 26, in the belt-like member 10-5 the outer periphery of each product is cut along a dashed line RC. At this moment, the outer periphery cut line RC is formed so as not to cut the section indicated by CS between the products.

Figure 27:
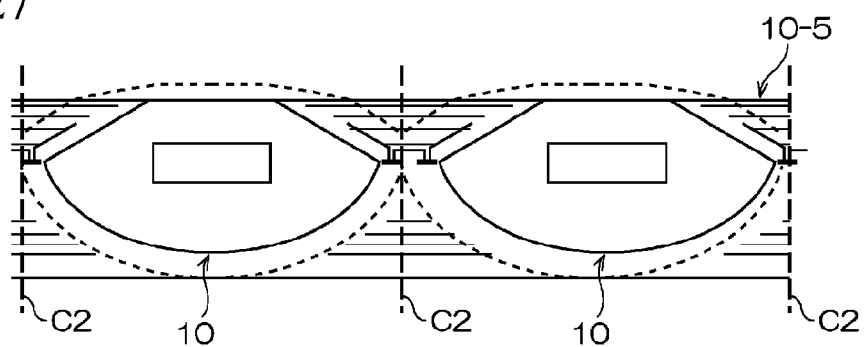
FIG. 27 is view showing the cutting process that is performed in a process of producing the breast-milk pad of FIG. 1.

Next, as shown in FIG. 27, the belt-like material 10-5 is cut along a cutting line C2 between the continuous breast-milk pad 10 of the belt-like member 10-5. Note that the outer periphery and the cutting line C2 may be cut simultaneously.

Figure 28:
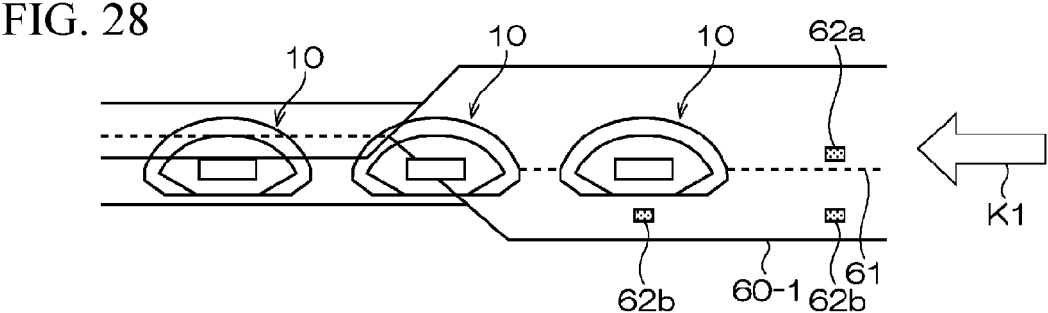
FIG. 28 is view showing a wrapping process that is performed in a process of producing the breast-milk pad of FIG. 1.

In this manner, each breast-milk pad 10 is formed. As shown in FIG. 28, while a belt-like material 60-1 for individually wrapping the breast-milk pads 10 that is provided beforehand with a perforated line 61 for opening the belt-like material 60-1 is sent along the conveyance direction K1, the completed breast-milk pads 10 are placed on the belt-like material 60-1 at regular intervals, then the belt-like member 60-1 is folded up by the folding means, and the overlapping part is sealed, whereby the breast-milk pads 10 are stored in the folded belt-like material 60-1. At this moment, the belt-like material 60-1 for wrapping the breast-milk pads 10 can include fixing adhesives 62a, 62b which are applied beforehand to positions corresponding to the release papers 19a, 19a attached to the back sheet 13, respectively, to adhere the release papers 19a. The release papers 19a are removed so that the temporary adhering portions 19, 19 are exposed when an individual package 60. Note that, by the release processing is performed beforehand on an inner surface of the wrapping belt-like member 60-1, the breast-milk pad 10 may be formed without using the release papers 19a.

Figure 29:
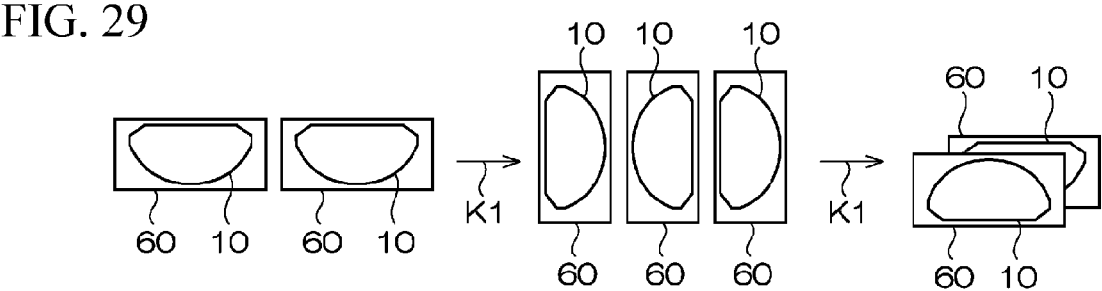
FIG. 29 is view showing the wrapping process that is performed in a process of producing the breast-milk pad of FIG. 1.

Next, as shown in FIG. 29, the breast-milk pads 10 that are produced continuously can be sent in the direction of K1 so as to be stored in the individual package 60 in different directions, and then packed in a product wrapping body, which is not shown.

Note that, for example, two breast-milk pads 10 may be disposed so as to be arranged vertically in the same direction on the wrapping belt-like member 60-1 shown in FIG. 28, the breast-milk pads 10 may be rotated 90 degrees and disposed on the wrapping belt-like member 60-1, and another wrapping belt-like member may be superposed thereon so that the two breast-milk pads 10 corresponding to the breasts are individually packaged, and thereafter the belt-like member 60-1 may be folded back using the folding board or the like so that the breast-milk pads 10 are overlapped alternately and stored as shown in FIG. 29.

Moreover, the depth of the dome shape of each breast-milk pad 10 can be configured according to the size of the user's breast by changing one or more of the following:, the angle of each of the cutout portions 22 formed in the process of producing the cutout portions 22 shown in FIG. 19; the angle of the sealing line 25 (H2) shown in FIG. 24, which is generated in a process of applying the sealing line 25; and the cutting line of the outer peripheral cut line RC shown in FIG. 26 may be changed, etc. When the breast-milk pad 10 is formed to have, for example, a deep dome shape, it may be produced so as to have large angle cutout portions 22 or the like, and when the breast-milk pad 10 is formed to have a shallow dome shape, it may be produced so as to have relatively smaller angle cutout portions 22 or the like.

Figure 30:
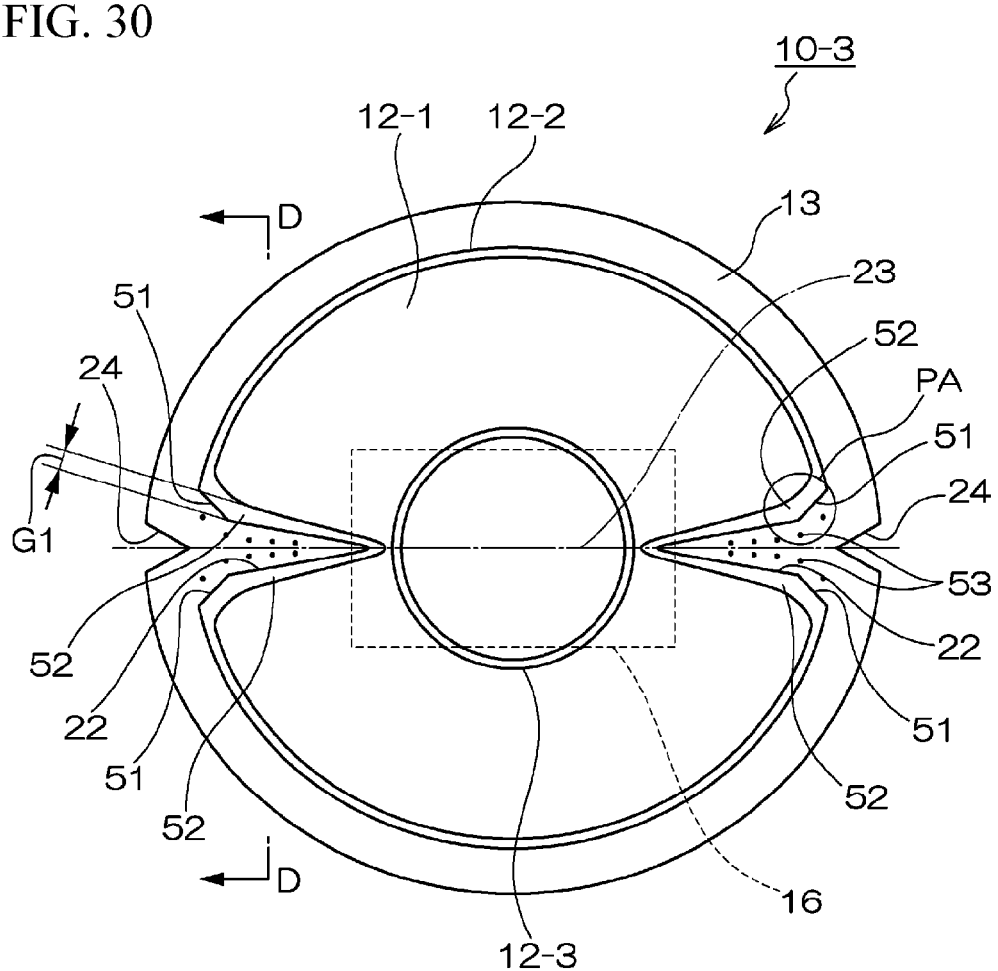
FIG. 30 is a schematic expanded view in which the breast-milk pad according to a fourth embodiment of the presently disclosed subject matter is viewed from the inner side thereof.
Figure 31:
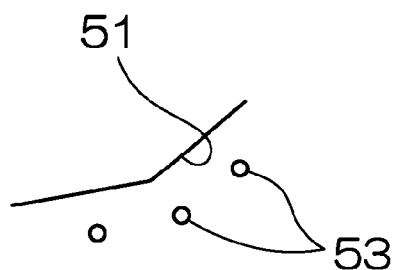
FIG. 31 is a partial enlarged view showing a section shown by reference numeral PA in FIG. 30.
Figure 31:
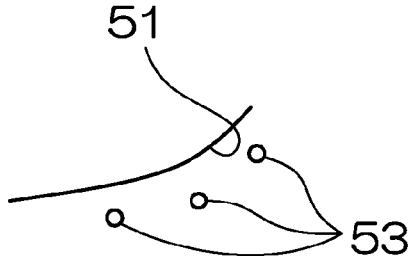
Figure 32:
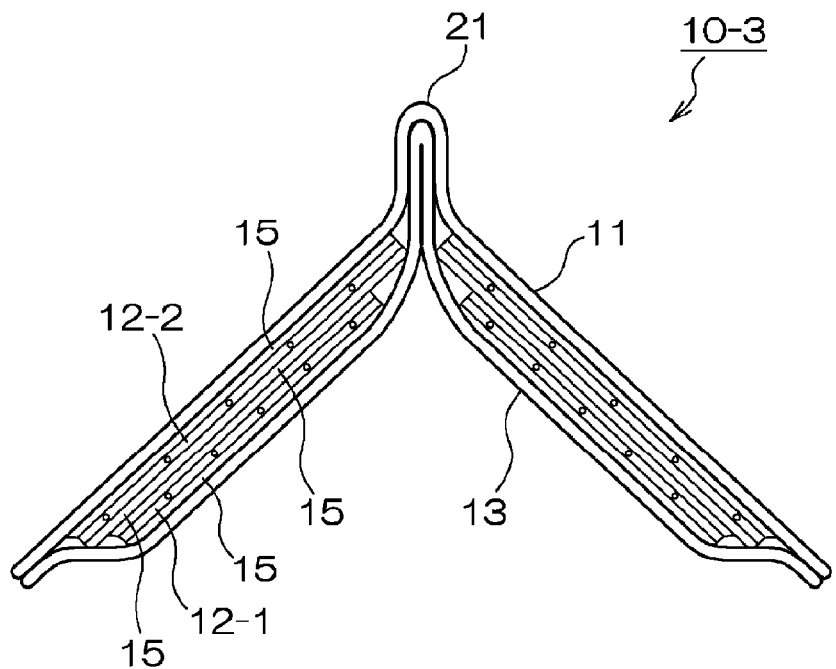
FIG. 32 is an end view that is cut along line D-D of FIG. 30.

FIG. 30 through FIG. 32 show a fourth embodiment of the breast-milk pad. In the fourth embodiment, the sections with the same reference numerals as those of the breast-milk pad of FIG. 1 are configured in the same way, hence their overlapping explanations are omitted and the differences are mainly described hereinafter.

FIG. 30 is a schematic expanded view in which a breast-milk pad 10-3 according to the fourth embodiment is viewed from the inner side thereof. FIG. 31 a partial enlarged view showing a section shown by reference numeral PA in FIG. 30. FIG. 32 is an end view that is cut along line D-D of FIG. 30.

In this breast-milk pad 10-3, two absorbers, i.e., the absorber 12-1 and an absorber 12-2, which are wrapped by the tissues 15 individually, are stacked, as shown in FIG. 30 and FIG. 32. Specifically, as described with reference to FIG. 20, a plurality of absorbers can be superposed so as to be able to absorb a great amount of liquid and to obtain a soft feel.

In this regard, at the cutout portions 22, an outer edge of the absorber 12-2 which forms a lower layer is configured to be larger than that of the absorber 12-1 forming an upper layer on the user's skin side, and the area shown by G1 is formed into an inclined surface or an inclined step portion. Accordingly, when heat-sealing shown in, for example, FIG. 9 is performed for forming the bonding portions 21 as shown in FIG. 32, edge portions of a plurality of absorbers that are superposed to obtain a thick layer form gentle steps, so that the bonding portions 21 can be bonded sufficiently and the breast-milk pad is effectively prevented from being displaced during use. Note that this inclined step portion G1 may be cut and formed to incline so that, even when the absorber 12 only includes one layer, the width of the top sheet 13 of the absorber 12 is formed wide and gradually narrows toward the back sheet 15.

Moreover, in this breast-milk pad 10-3, an embossed portion 12-3 is formed by compressing the absorbers 12-1, 12-2 through the absorbing/dispersing layer 16 from the top sheet 13 side.

This embossed portion 12-3 is a compressing groove which is formed into a precise circle on the inner side of the cutout portions 22 by heating and compressing the absorbers 12-1, 12-2 from the top sheet 13 side. The compressed groove is in the form of a circle larger than the papilla so as not to contact and irritate the papilla, and is configured such that the user can easily find the position contacting the papilla. Also, the absorbers 12-1, 12-2, the absorbing/dispersing layer 16 and the top sheet 13 can be held integrally by this embossed portion 12-3 and the direction of the flow of absorbed breast milk is controlled, hence, by disposing the embossed portion 12-3 in the vicinity of the peaks of the cutout portions 22. The absorbed breast milk is thus prevented from leaking from the cutout portions 22 and can be guided in another direction.

In addition, a large opening portion 51 is formed on the outer peripheral edge of each of the cutout portions 22 formed by cutting out the absorbers 12-1, 12-2. The large opening portion 51 is provided such that the angle formed by the outer edge of the absorbers is made larger than that formed by an other outer edge of each of the cutout portions 22 with respect to the folding line 23.

In addition, on the inner side of each one of the cutout portions 22 in this embodiment, a strong sealing portion 53, which is a sealing section for reinforcing the bonding between the top sheet 13 and the back sheet 11, is formed.

Specifically, an outer edge of the large opening portion 51 can be chamfered to form a straight line as shown in FIG. 31(a), or can be formed into a curved line as shown in FIG. 31(b). The strong sealing portion 53 is configured by forming in, for example, a section that is slightly away from the outer edge of the large opening portion 51, a section subjected to heat sealing in the form of dots or a line. An outside end portion of the strong sealing portion 53 is disposed within an area of an extended line that is formed when the large opening portion 51 is not formed.

Accordingly, the breast-milk pad 10-3 not only can achieve the effects described in the other embodiments but also improve the action of forming the dome shape, because the strong sealing portion 53 functions similarly to the sealing line 25 described in detail using FIG. 5 and FIG. 6, and the large opening portion 51 is formed so that the outer end portion of the strong sealing portion 53 is disposed in the area of the large opening portion 51, whereby the strong sealing portion 53 is bonded the breast-milk pad 10 is opened from the folded state. Moreover, the breast-milk pad 10-3 acts so as not to expose the section that is not capable of absorbing and retaining liquid, to the top sheet 13, hence the leaked breast milk can be absorbed securely.

Figure 33:
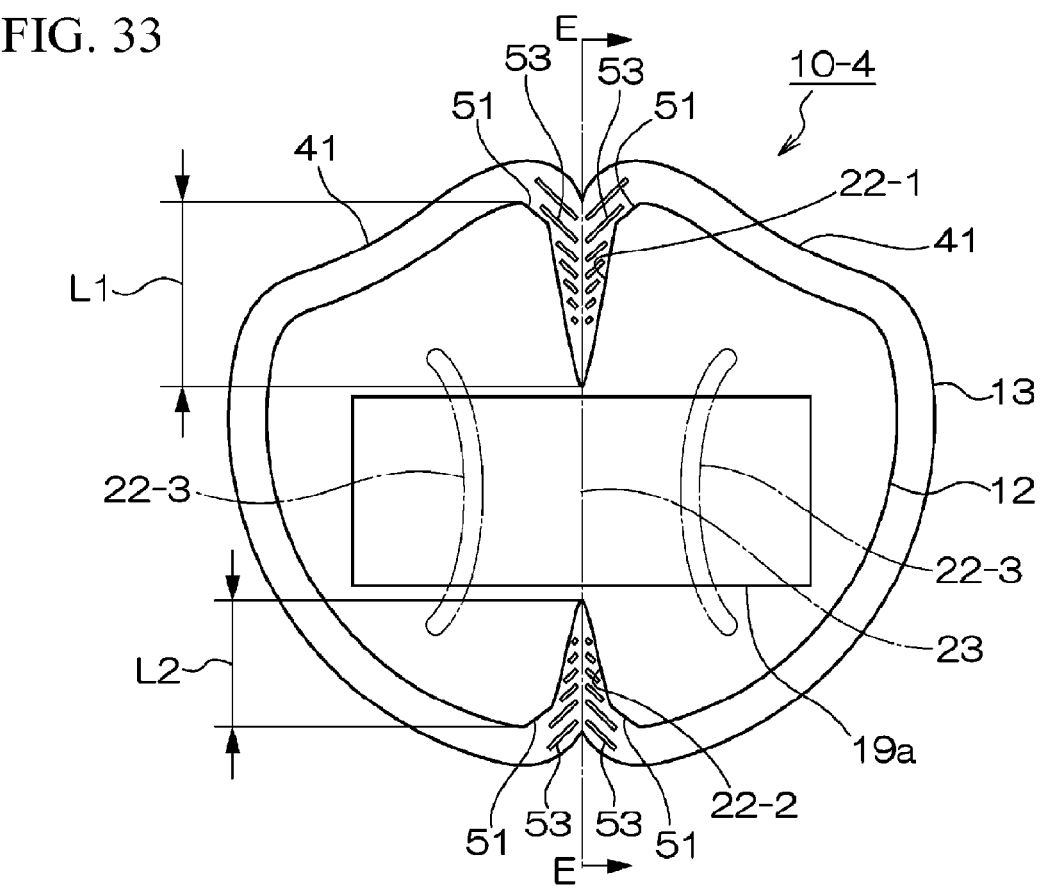
FIG. 33 is a schematic expanded view in which the breast-milk pad according to a fifth embodiment of the presently disclosed subject matter is shown from the outer side thereof.
Figure 34:
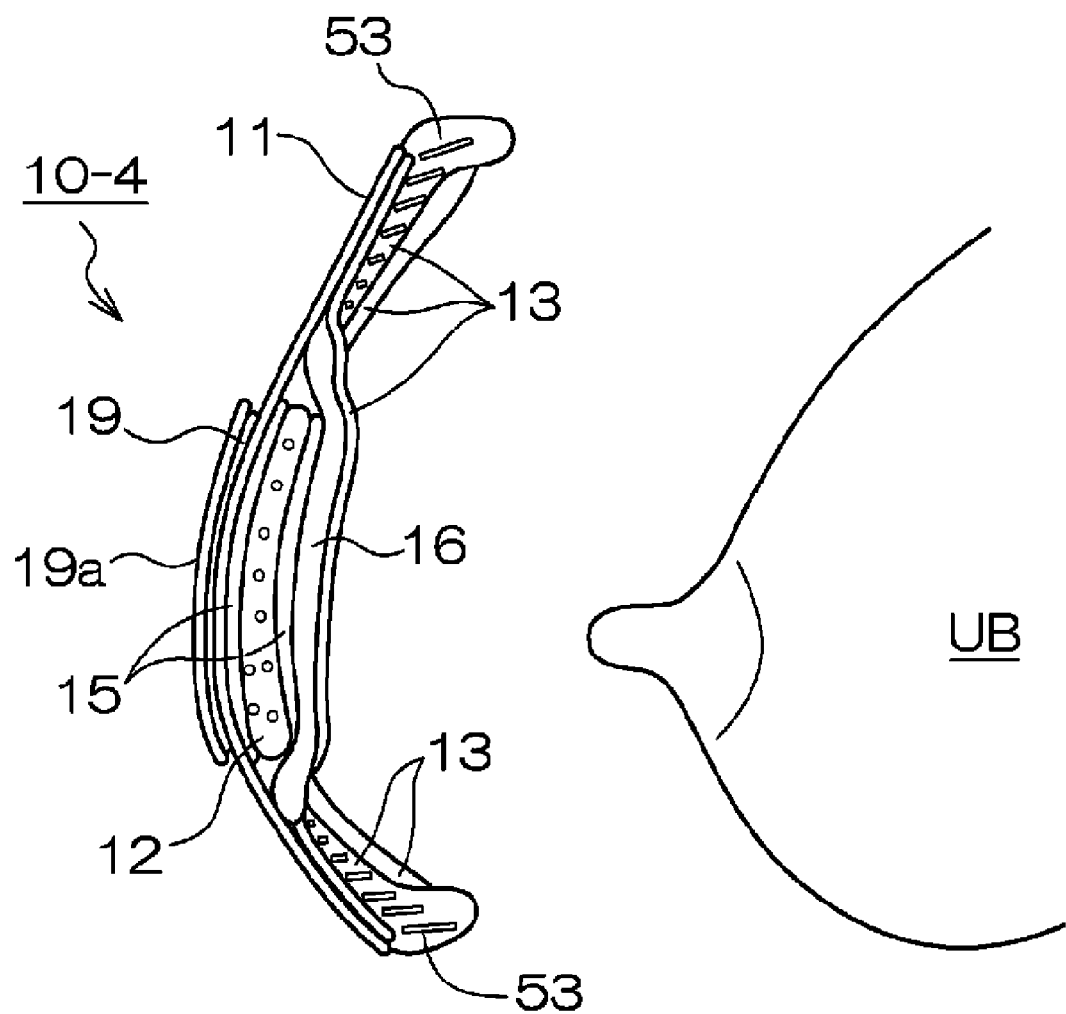
FIG. 34 is an end view that is cut along line E-E of FIG. 33.

FIG. 33 and FIG. 34 show a fifth embodiment of the breast-milk pad. In the fifth embodiment, the sections with the same reference numerals as those of the breast-milk pad of FIG. 1 and the breast-milk pad of the fourth embodiment are configured in the same way, hence their overlapping explanations are omitted and the differences are mainly described hereinafter.

FIG. 33 is a schematic expanded view in which a breast-milk pad 10-4 according to the fifth embodiment is viewed from the outside thereof, and FIG. 34, which is an end view that is cut along line E-E of FIG. 33, shows a breast UB of the user, along with the pad in a state in which the bonding portion cut is in the bonded state.

In these drawings, the breast-milk pad 10-4 has the outer edge cut portions 41, 41 as shown in FIG. 12, and is attached to the inner side of the brassiere B as described with reference to FIG. 12.

At this moment, in the present embodiment, because the temporary adhering portion 19 provided within the release paper 19a is disposed horizontally long such as to straddle the folding line 23, the breast-milk pad can be fixed securely within the brassiere B.

Moreover, in this breast-milk pad 10-4 the absorber 12 is pressed from the top sheet 13 side to form embossed portions 22-3, 22-3 on the right and left of the absorber 12. The embossed portions 22-3 are curved compressed grooves that are formed such that each end portion thereof stretches outward in the right and left areas, with the folding line 23 therebetween, so as not to contact the papilla and so as not to straddle the folding line 23 connecting the peaks of the cutout portions 22. The breast-milk pad 10-4 can be easily deformed by the embossed portions 22-3 so that following can be accomplished: maintenance of the dome shape can be assisted; the breast milk can be prevented from leaking from the right and left; and the absorber 12, the absorbing/dispersing layer 16 and the like can be integrally held.

In this breast-milk pad, the pair of cutout portions 22-1, 22-2 are positioned corresponding to the upper and lower positions in the attached state of the product, as shown. For this reason, the folding line 23 is disposed in a vertical direction as shown. Moreover, the strong sealing portion 53 of the bonding portion 21 is configured not in the form of dots but in the form of a plurality of inclined lines such that the length of each of the inclined lines increases toward the outer periphery from the center in each of the cutout portions 22-1, 22-2, and the outer end portion of the strong sealing portion 53 disposed corresponding to the large opening portion 51 is disposed in the area of the large opening portion 51.

More specifically, of the two cutout portions, in this embodiment the length L1 of the upper cutout portion 22-1 is formed to be longer than the length L2 of the lower cutout portion 22-2. Note that, instead of changing the length of the cutout portions 22-1, 22-2, the cutout portions may be configured such that the width of the lower cutout portion 22-2 is made wider than the width of the upper cutout portion 22-1.

The present embodiment is configured as above, in which the two cutout portions 22-1, 22-2 and the bonding portions 21 are formed corresponding to the upper and lower positions, and the folding line 23 is formed in the vertical direction, whereby the vertical rigidity of the breast-milk pad 10-4 is improved. Accordingly, the breast-milk pad 10-4 is made rigid enough against the vertical movement of the cup even when the cup of underwear, particularly the brassiere B shown in FIG. 12, is opened vertically at the time of breast-feeding. Hence, a situation can be prevented in which the shape of the product is not easily sustained and is deformed.

In addition, the length L1 of the upper cutout portion 22-1 is formed to be longer than the length L2 of the lower cutout portion 22-2, and the width of the lower cutout portion 22-2 is formed wide.

For this reason, as shown in FIG. 34, by bonding the bonding portions that are the inner surfaces of the top sheet 13 overlapping on each other at the cutout portions 22-1, 22-2, the dome shape that is formed can conform to the shape of the breast UB.

Specifically, when the breast UB is relatively large, the lower part thereof is steep while the upper part gently rises as shown, but the breast-milk pad 10-4 can suitably cover such breast UB.

Note that the other effects of the breast-milk pad 10-4 may be the same as those of each of the embodiments described above.

The presently disclosed subject matter is not limited to the above-described embodiments.

For example, other objects may be stored on the inner side of the back sheet 11 or top sheet 13 besides only the absorber 12, the sub-layer 16 and the tissues 15.

Two absorbers may be stored. For example, arched grooves that extend radially or outward in an opposing fashion may be embossed on the absorber. Moreover, the shape of the breast-milk pad 10 may not only be a circular shape but can also be a large tear shape at its lower side, a triangular shape, an elliptical shape, or an oblong shape, etc. Furthermore, instead of disposing the bonding portions 21 or the folding line 23 in substantially the middle in the horizontal direction or vertical direction, they may be disposed in a position located slightly downward, or may be configured such that the center is risen at the lower side. The peaks at the inner ends of the cutout portions 22 may not only be cut out into a sharp point but also into a round shape so that the peaks at the inner ends of the cutout portions can be deformed easily when the dome shape is formed. In addition, the components of each of the embodiments described above may be selected arbitrarily and combined.

While the invention has been described in detail with reference to exemplary embodiments thereof, it will be apparent to one skilled in the art that various changes can be made, and equivalents employed, without departing from the scope of the invention. The foregoing description of embodiments of the invention has been presented for purposes of illustration and description. It is not intended to be exhaustive or to limit the invention to the precise form disclosed, and modifications and variations are possible in light of the above teachings or may be acquired from practice of the disclosed subject matter. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned conventional documents is incorporated by reference herein.

The invention claimed is:

1. A breast pad, comprising:
   a back sheet configured to prevent permeation of liquid;
   a liquid permeable top sheet configured to contact a user's body; and
   an absorber that is disposed between the back sheet and the top sheet and configured to absorb and retain liquid that permeates the top sheet,
   wherein the top sheet and the back sheet are bonded to each other at an outer peripheral portion of the top sheet and the back sheet, cutout portions defined by cuts in the absorber are located at positions facing each other and at an outer peripheral portion of the absorber such that a cutout width of each of the cutout portions gradually narrows down inwardly towards a central area of the absorber, the top sheet and the back sheet are bonded to each other at the cutout portions, and the breast pad includes bonding portions located at and configured to bond inner facing surfaces of the top sheet together, the inner facing surfaces of the top sheet being superposed at each of the cutout portions when the breast pad is folded up along a folding line connecting the cutout portions so that the top sheet forms the inner surfaces, and
   an absorbing/dispersing layer with higher density than the absorber and located between the absorber and the top sheet, wherein the absorbing/dispersing layer is disposed on an inner side of each bonding portion.

2. The breast pad according to claim 1, wherein the top sheet includes a thermal fusion material and is configured to be heated from the back sheet side and fused at the cutout portions when the breast pad is folded.

3. The breast pad according to claim 1, wherein the cutout portions are formed at four sections with two pairs of cutout portions facing each other and located at an outer edge portion of the absorber and, the absorber being folded along a folding line connecting cutout portions which face each other such that the top sheet forms the inner surfaces and the entire pad is folded into three.

4. The breast pad according to claim 1, wherein at least one outer edge cut portion is formed in an outer edge portion of the pad by removing a portion of the top sheet, back sheet and the absorber.

5. The breast pad according to claim 1, wherein when the pad is opened into a substantially dome shape, a sealing line is located in the cutout portions to form the bonding portions such that a gap located between edges that define the cutout portions is substantially non-existent and imperceptible by the user.

6. The breast pad according to claim 1, wherein an outer edge portion where only the top sheet and the back sheet are superposed and an area in which the absorber is interposed between the top sheet and the back sheet are bonded together, and bonding is achieved by being sandwiched and pressed.

7. The breast pad according to claim 1, wherein fibers configuring the top sheet are oriented in an aligned manner along a direction in which the folding line extends.

8. The breast pad according to claim 1, wherein at least one of the cutout portions has a large opening portion located at an outer edge of the pad such that an angle of an edge of the opening portion formed with respect to the folding line is relatively large, and a seal configured to reinforce the bond between the top sheet and the back sheet is provided on an inner side of the large opening portion, the inner side being closer to a central portion of the pad than is the outer peripheral portion of the top sheet and back sheet.

9. The breast pad according to claim 1, wherein the cutout portions include an upper cutout portion and a lower cutout portion corresponding to an upper and a lower position, respectively, of the pad when the pad is in an attached state with respect to a user.

10. The breast pad according to claim 9, wherein the upper cutout portion is at least one of longer in length and narrower in width than the lower cutout portion, and wherein length is measured along a length axis extending from an outer perimeter of the pad to a central area of the pad, and width is measured substantially normal to the length axis.

11. The breast pad according to claim 1, wherein the cutout portions are formed in two sections facing each other at an outer edge portion of the absorber, and the breast pad is folded into two along the folding line.

12. The breast pad according to claim 1, wherein the bonding portions and the inner facing surface of the top sheet extend in a direction away from and substantially normal to the absorber and intersecting the cutout portions in the absorber.

13. A method for producing the breast pad according to claim 1, the method comprising:
    molding the absorber and cutting out portions of the absorber to form cutout portions facing each other and located at the outer periphery of the absorber, the cutout portions formed in such a manner that cutout width gradually narrows down from the outer periphery of the absorber inwardly towards the central portion of the absorber;
    stacking the molded absorber between the back sheet to prevent permeation of liquid and the liquid permeable top sheet;
    sealing the top sheet and the back sheet to constitute the outer periphery of the pad;
    folding the pad along the folding line connecting the cutout portions which face each other so that the top sheet forms inner surfaces facing each other; and
    bonding together the inner surfaces of the top sheet that face each other and are superposed at the cutout portions.

14. The method for producing a breast pad according to claim 13, wherein the bonding heat-seals an area along an outer edge of the absorber at least once, and further heat-seals a vicinity of an inner end of each of the cutout portions.

15. The method for producing a breast pad according to claim 13, further comprising:
    cutting the pad from a product unit including a plurality of partially manufactured pads.

16. The method for producing a breast pad according to claim 13, wherein bonding occurs when the pad is folded along the folding line.

17. The method for producing a breast pad according to claim 13, wherein bonding includes creating a seal line in the top sheet and back sheet located in the cutout portions of the absorber.

* * * * *